United States Patent [19]

Wiederkehr et al.

[11] 4,313,945
[45] Feb. 2, 1982

[54] 7-THIAZOLYL-ACETAMIDO-CEPHEM DERIVATIVES WITH TERMINAL AMINOCARBOXYLIC ACID GROUPING

[75] Inventors: René Wiederkehr, Pfeffingen; Riccardo Scartazzini, Basel, both of Switzerland

[73] Assignee: Ciba-Geigy Corporation, Ardsley, N.Y.

[21] Appl. No.: 93,645

[22] Filed: Nov. 13, 1979

[30] Foreign Application Priority Data

Nov. 23, 1978 [CH] Switzerland .................. 12025/78

[51] Int. Cl.³ .................. A61K 31/545; C07D 501/20
[52] U.S. Cl. .................. 424/246; 544/21; 544/22; 544/25; 544/27; 544/28; 548/195; 548/196
[58] Field of Search .................. 544/28, 21, 22, 25, 544/27; 424/246

[56] References Cited

U.S. PATENT DOCUMENTS

| | | | |
|---|---|---|---|
| 4,007,173 | 2/1977 | Hoover et al. | 544/26 |
| 4,098,888 | 7/1978 | Ochiai et al. | 544/28 |
| 4,166,115 | 8/1979 | Takaya et al. | 424/246 |
| 4,202,893 | 5/1980 | Heymes et al. | 544/28 |
| 4,242,509 | 12/1980 | Lunn | 544/21 |

FOREIGN PATENT DOCUMENTS 500 2/1979 European Pat. Off. .

Primary Examiner—Paul M. Coughlan, Jr.
Attorney, Agent, or Firm—Prabodh I. Almaula

[57] ABSTRACT

The invention relates to aminothiazolacetamido-3-cephem-4-carboxylic acid compounds of the formula

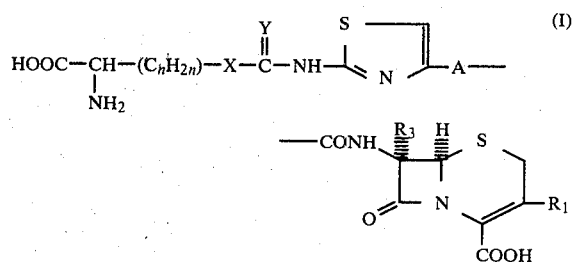

in which
the index n represents an integer of 1 to 4,
X represents oxygen, sulphur, an —NH— group or the direct bond,
Y represents oxygen or sulphur,
A represents methylene or methylene substituted by amino, hydroxy, carboxyl, sulpho, oxo, or the group =N—O—R° in which R° represents hydrogen or optionally substituted lower alkyl,
$R_1$ represents hydrogen, lower alkyl, an esterified or etherified hydroxy or mercapto group, halogen, formyl or a group of the formula —CH$_2$—R$_2$ in which R$_2$ represents an esterified or etherified hydroxy or mercapto group or a quaternary ammonium group, and
$R_3$ represents hydrogen or methoxy,
in which functional groups are optionally present in protected form,
salts of such compounds with acidic and/or basic groups, processes for the manufacture of these compounds, pharmaceutical agents containing such substances and their therapeutic use.

The compounds have an antibiotic activity and can be used for combating infections.

The invention also relates to new intermediates for the manufacture of the afore-mentioned compounds, processes for their manufacture and their use.

12 Claims, No Drawings

7-THIAZOLYL-ACETAMIDO-CEPHEM DERIVATIVES WITH TERMINAL AMINOCARBOXYLIC ACID GROUPING

The invention relates to new aminothiazolacetamido-3-cephem-4-carboxylic acid compounds and their salts, processes for their manufacture, pharmaceutical agents having an antibiotic activity that contain these compounds and their therapeutic use for treating infections, and new intermediates and their manufacture.

A number of aminothiazolacetamido-3-cephem-4-carboxylic acid compounds have already become known as effective antibiotics.

The problem underlying the present invention is to manufacture new 7β-aminothiazolacetamido-3-cephem-4-carboxylic acid compounds in which the amino group is substituted by a radical having a terminal α-aminocarboxylic acid grouping. The new compounds are distinguished by an excellent action against normal and resistant bacteria.

The invention also relates to the novel substituted aminothiazolacetic acids and their reactive functional derivatives in which functional groups are optionally protected, which are to be used as starting materials, and to processes for their manufacture.

The invention relates especially to aminothiazolacetamido-3-cephem-4-carboxylic acid compounds of the formula

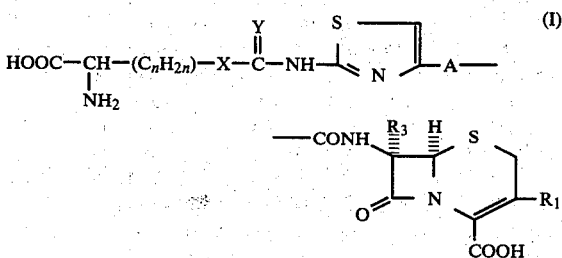

in which
the index n represents an integer of 1 to 4,
X represents oxygen, sulphur, an —NH— group or the direct bond,
Y represents oxygen or sulphur,
A represents methylene or methylene substituted by amino, hydroxy, carboxyl, sulpho, oxo, or the group =N—O—R$^o$ in which R$^o$ represents hydrogen or optionally substituted lower alkyl,
R$_1$ represents hydrogen, lower alkyl, an esterified or etherified hydroxy or mercapto group, halogen, formyl, or a group of the formula —CH$_2$—R$_2$ in which R$_2$ represents an esterified or etherified hydroxy or mercapto group or a quaternary ammonium group, and
R$^3$ represents hydrogen or methoxy,
wherein functional groups are optionally present in protected form,
salts of such compounds with acidic and/or basic groups, processes for the manufacture of these compounds, pharmaceutical agents containing such substances and their therapeutic use.

In the present description of the invention the term "lower" in groups such as lower alkyl, lower alkylene, lower alkoxy, lower alkanoyl and the like, means that the corresponding groups, unless expressly defined otherwise, contain up to 7, preferably up to 4, carbon atoms.

A —(C$_n$H$_{2n}$)— group is a branched or unbranched alkylene chain and is especially methylene, ethylene, trimethylene or tetramethylene and also, for example, ethylidene, propylidene, propylene, butylidene or isobutylidene.

In a =N—O—R$^o$ group, when R$^o$ represents an optionally substituted lower alkyl it contains 1–4 carbon atoms. Substituents of such a lower alkyl group R$^o$ are, for example, lower alkoxy, such as methoxy; halogen, such as fluorine, chlorine or bromine; hydroxy or acylated hydroxy, such as lower alkanoyloxy, for example acetoxy; sulpho; and especially free or also esterified carboxy.

Representative groups R$^o$ are, for example, methyl, ethyl, propyl, butyl, methoxymethyl, methoxyethyl, such as 2-methoxyethyl, 3-methoxypropyl, 4-methoxybutyl, 2-haloethyl, such as 2-chloroethyl, 3-halopropyl, such as 3-chloropropyl, or 4-halobutyl, such as 4-chlorobutyl, 2-hydroxyethyl, 3-hydroxypropyl or 4-hydroxybutyl, in which the hydroxy group may be acylated, for example, by lower alkanoyl, such as acetyl, 2-sulphoethyl, 3-sulphopropyl, 2-carboxyethyl, 3-carboxypropyl or 4-carboxybutyl, in which the carboxy group may be esterified, for example by lower alkyl, such as methyl or ethyl.

A lower alkyl group R$_1$ contains 1–4 carbon atoms and is, for example, ethyl, propyl, butyl or especially methyl.

An esterified hydroxy or mercapto group R$_1$ is esterified, for example, by a lower aliphatic carboxylic acid or by an optionally N-substituted carbamic acid.

Hydroxy groups R$_1$ esterified by lower aliphatic carboxylic acids are especially lower alkanoyloxy, especially acetoxy, or formyloxy, propionoxy, valeryloxy, hexanoyloxy, heptanoyloxy or pivaloyloxy.

Mercapto groups R$_1$ esterified by lower aliphatic carboxylic acids are lower alkanoylthio, such as acetylthio, formylthio, propionylthio, valeroylthio, hexanoylthio, heptanoylthio or pivaloylthio.

In a hydroxy or mercapto group R$_1$ esterified by an optionally N-substituted carbamic acid, the N-substituents are lower alkyl optionally substituted by halogen, for example chlorine, or by lower alkanoyl, for example acetyl or propionyl, for example methyl, ethyl, 2-chloroethyl or 2-acetoxyethyl. Hydroxy groups R$_1$ esterified in this manner are, for example, carbamoyloxy, N-methylcarbamoyloxy, N-ethylcarbamoyloxy, N-(2-chloroethyl)carbamoyloxy or N-(2-acetoxyethyl)carbamoyloxy. Corresponding esterified mercapto groups R$_1$ are, for example, carbamoylthio, N-methylcarbamoylthio, N-ethylcarbamoylthio, N-(2-chloroethyl)carbamoylthio or N-(2-acetoxyethyl)carbamoylthio.

Etherified hydroxy and mercapto groups R$_1$ are etherified, for example, by an optionally substituted aliphatic or araliphatic hydrocarbon radical, and are especially lower alkoxy, especially having 1–4 carbon atoms, particularly methoxy, as well as ethoxy, n-propoxy or isopropoxy, or straight-chain or branched butoxy, benzyloxy or diphenylmethoxy or lower alkylthio, preferably having 1–4 carbon atoms, especially methylthio, as well as ethylthio, n-propylthio or isopropylthio, or also straight-chain or branched butylthio, benzylthio or diphenylmethylthio.

Etherified mercapto groups R$_1$ are etherified especially by an optionally substituted heterocyclic radical bonded by a ring carbon atom to the mercapto group and having 1 to 4 ring nitrogen atoms and optionally a further ring hetero atom from the group oxygen and sulphur.

Heterocyclic radicals of this type are especially optionally substituted, for example by the substituents mentioned below, monocyclic, five-membered diazacyclic, triazacyclic, tetrazacyclic, thiazacyclic, thiadiazacyclic, thiatriazacyclic, oxazacyclic or oxadiazacyclic radicals of aromatic character.

Substituents of such heterocyclyl radicals are, inter alia, lower alkyl, especially methyl, as well as ethyl, n-propyl and isopropyl, or straight-chain or branched butyl; or lower alkyl substituted by hydroxy, by esterified hydroxy, such as lower alkanoyloxy, by halogen, such as chlorine, by carboxy, by esterified carboxy, such as lower alkoxycarbonyl, by sulpho, by amidated sulpho, by amino, by mono- or di-lower alkylamino, by acylamino, such as lower alkanoylamino or by substituted lower alkanoylamino, such as lower alkanoylamino substituted by carboxy or halogen, for example 2-hydroxyethyl, 2-acetoxyethyl, 2-chloroethyl, carboxymethyl, 2-carboxyethyl, ethoxycarbonylmethyl, 2-ethoxycarbonylethyl, sulphomethyl, 2-sulphoethyl, sulphamylmethyl, 2-sulphamylethyl, 2-aminoethyl, 2-dimethylaminoethyl or 2-acetylaminoethyl. Other substituents of the heterocyclic radical are cycloalkyl, for example cyclopentyl or cyclohexyl; aryl, such as phenyl optionally substituted by halogen, for example chlorine, or by nitro; aryl-lower alkyl, for example benzyl; or heterocyclyl, such as furyl, for example fur-2-yl, thienyl, for example thien-2-yl, or oxazolyl, for example oxazol-2-yl or oxazol-5-yl; or functional groups, such as halogen, for example fluorine, chlorine or bromine, optionally substituted amino, such as amino optionally mono-substituted or di-substituted by lower alkyl, for example amino, methylamino or dimethylamino, acylamino, such as lower alkanoylamino or lower alkanoylamino substituted by halogen or carboxy, such as acetylamino, 3-chloropropionylamino or 3-carboxypropionylamino, nitro, hydroxy, lower alkoxy, for example methoxy, ethoxy, n-butoxy or 2-ethylhexyloxy, or optionally functionally modified carboxy, such as carboxy, esterified carboxy, such as lower alkoxycarbonyl, for example methoxycarbonyl or ethoxycarbonyl, optionally substituted, such as N-mono-lower alkylated or N,N-di-lower alkylated carbamoyl, for example N-methylcarbamoyl or N,N-dimethylcarbamoyl, or cyano, as well as oxo or oxido; wherein one or more such substituents that are bonded especially to ring carbon atoms or alternatively, especially lower alkyl and oxido, to ring nitrogen atoms, may be present.

Preferred mercapto groups $R_1$ etherified by a heterocyclic radical, in which the heterocyclic radical represents a corresponding monocyclic, five-membered radical, are, inter alia, imidazolylthio, for example imidazol-2-ylthio; triazolylthio optionally substituted by lower alkyl and/or phenyl, for example 1H-1,2,3-triazol-4-ylthio, 1-methyl-1H-1,2,3-triazol-4-ylthio, 1H-1,2,4-triazol-3-ylthio, 5-methyl-1H-1,2,4-triazol-3-ylthio, 3-methyl-1-phenyl-1H-1,2,4-triazol-5-ylthio, 4,5-dimethyl-4H-1,2,4-triazol-3-ylthio or 4-phenyl-4H-1,2,4-triazol-3-ylthio; especially tetrazolylthio optionally substituted as stated, for example, 1H-tetrazol-5-ylthio, 1-methyl-1H-tetrazol-5-ylthio, 1-carboxymethyl-1H-tetrazol-5-ylthio, 1-(2-carboxyethyl)-1H-tetrazol-5-ylthio, 1-sulphomethyl-1H-tetrazol-5-ylthio, 1-(2-sulphoethyl)-1H-tetrazol-5-ylthio, 1-(2-dimethylaminoethyl)-1H-tetrazol-5-ylthio, 1-phenyl-1H-tetrazol-5-ylthio or 1-(4-chlorophenyl)-1H-tetrazol-5-ylthio; thiazolylthio or isothiazolylthio optionally substituted by lower alkyl or thienyl, for example thiazol-2-ylthio, 4-(thien-2-yl)thiazol-2-ylthio, 4,5-dimethylthiazol-2-ylthio, isothiazol-3-ylthio, isothiazol-4-ylthio or isothiazol-5-ylthio; especially also thiadiazolylthio optionally substituted as stated, for example 1,2,3-thiadiazol-4-ylthio, 1,2,3-thiadiazol-5-ylthio, 1,3,4-thiadiazol-2-ylthio, 2-methyl-1,3,4-thiadiazol-5-ylthio, 2-(3-carboxypropionylamino)-1,3,4-thiadiazol-5-ylthio, 1,2,4-thiadiazol-5-ylthio or 1,2,5-thiadiazol-3-ylthio; thiatriazolylthio, for example 1,2,3,4-thiatriazol-5-ylthio; oxazolylthio or isoxazolylthio optionally substituted as stated, for example oxazol-5-ylthio, 4-methyloxazol-5-ylthio, oxazol-2-ylthio, 4,5-diphenyloxazol-2-ylthio or 3-methylisoxazol-5-ylthio; or oxadiazolylthio optionally substituted as stated, for example 1,2,4-oxadiazol-5-ylthio, 2-methyl-1,3,4-oxadiazol-5-ylthio, 2-phenyl-1,3,4-oxadiazol-5-ylthio, 5-(4-nitrophenyl)-1,3,4-oxadiazol-2-ylthio or 2-(thien-2-yl)-1,3,4-oxadiazol-5-ylthio.

Preferred mercapto groups $R_1$ etherified by a heterocyclic radical, in which the heterocyclic radical represents a corresponding monocyclic six-membered radical or a corresponding partially saturated radical are, inter alia, 1-oxidopyridylthio optionally substituted by halogen, for example 1-oxidopyrid-2-ylthio or 4-chloro-1-oxidopyrid-2-ylthio; pyridazinylthio optionally substituted by hydroxy, for example 3-hydroxypyridazin-6-ylthio; N-oxidopyridazinylthio optionally substituted by lower alkyl, lower alkoxy or halogen, for example 2-oxidopyridazin-6-ylthio, 3-chloro-1-oxidopyridazin-6-ylthio, 3-methyl-2-oxidopyridazin-6-ylthio, 3-methoxy-1-oxidopryidazin-6-ylthio, 3-ethoxy-1-oxidopyridazin-6-ylthio, 3-n-butoxy-1-oxidopyridazin-6-ylthio or 3-(2-ethylhexyloxy)-1-oxidopyridazin-6-ylthio; or 2-oxo-1,2-dihydropyrimidinylthio optionally substituted by lower alkyl, amino, di-lower alkylamino or carboxy, for example 2-oxo-1,2-dihydropyrimidin-4-ylthio, 6-methyl-2-oxo-1,2,-dihydropyrimidin-4-ylthio, 5-methyl-2-oxo-1,2-dihydropyrimidin-4-ylthio, 6-amino-2-oxo-1,2-dihydropyrimidin-4-ylthio, 6-dimethylamino-2-oxo-1,2-dihydroypyrimidin-4-ylthio, 5-carboxy-2-oxo-1,2-dihydropyrimidin-4-ylthio or 6-carboxy-2-oxo-1,2-dihydropyrimidin-4-ylthio.

When $R_1$ represents a halogen atom it is fluorine, bromine, iodine or preferably chlorine.

Esterified and etherified hydroxy and mercapto groups $R_2$ are the same as the corresponding groups mentioned under $R_1$.

Quaternary ammonium groups $R_2$ are quaternary ammonium groups that are derived from tertiary organic bases, preferably from corresponding aliphatic amines or especially corresponding heterocyclic nitrogen bases, and are bonded via the nitrogen atom to the methylcarbon atom.

In a quaternary ammonium group $R_2$ that is derived from a tertiary organic base, the nitrogen atom is bonded to the methylcarbon atom and is accordingly present in quaternised, positively charged form. Quaternary ammonium groups are, inter alia, tri-lower alkylammonium, for example trimethylammonium, triethylammonium, tripropylammonium or tributylammonium; but especially monocyclic or bicyclic azacyclic ammonium groups of aromatic character having 1 or 2 ring nitrogen atoms and optionally one ring sulphur atom, optionally mono-substituted or poly-substituted by, for example, lower alkyl, such as methyl, hydroxy-lower alkyl, such as hydroxymethyl, amino, substituted sulphonamido, such as 4-aminophenylsulphonamido, hydroxy, halogen, such as fluorine, chlorine, bromine or iodine, halo-lower alkyl, such as trifluoromethyl, sulpho, optionally functionally modified carboxy, cyano, carbamoyl optionally N-mono-substituted or N,N-di-substituted by lower alkyl, for example methyl or ethyl, or by hydroxy-lower alkyl, for example hydroxymethyl, for example carbamoyl, N-methylcarbamoyl or N,N-dimethylcarbamoyl, hydrazinocarbonyl optionally N-substituted by lower alkyl, for example hydrazinocarbonyl, carboxy-lower alkyl, such as carboxy-methyl, lower alkanoyl, such as acetyl, or 1-lower alkylpyrrolidinyl, such as 1-methylpyrrolidin-2-yl; examples of such ammonium groups of aromatic character are pyrimidinium, pyridazinium, thiazolium, quinolinium and especially pyridinium.

Heterocyclic ammonium groups $R_2$ are especially pyridinium optionally containing lower alkyl, hydroxy-lower alkyl, amino, substituted sulphonamido, hydroxy, halogen, trifluoromethyl, sulpho, carboxy, lower alkoxycarbonyl, cyano, lower alkanoyl, 1-lower alkylpyrrolidinyl or carbamoyl optionally N-substituted by lower alkyl or hydroxy-lower alkyl, for example pyridinium 2-, 3- or 4-methylpyridinium, 3,5-dimethylpyridinium, 2,4,6-trimethylpyridinium, 2-, 3- or 4-ethylpyridinium, 2-, 3- or 4-propylpyridinium or especially 4-hydroxymethylpyridinium, or 2-amino- or 2-amino-6-methylpyridinium, 2-(4-aminophenylsulphonylamido)-pyridinium, 3-hydroxypyridinium, 3-fluoro-, 3-chloro-, 3-iodo- or especially 3-bromo-pyridinium, 4-trifluoromethylpyridinium, 3-sulphopyridinium, 2-, 3- or 4-carboxypyridinium or 2,3- or 3,4-dicarboxypyridinium, 4-methoxycarbonylpyridinium, 3-cyanopyridinium, 4-cyanopyridinium, 3-carboxymethylpyridinium, 3-acetylpyridinium, 4-acetylpyridinium, 3-(1-methylpyrrolidin-2-yl)pyridinium, and especially 4-carbamoylpyridinium, 3-carbamoylpyridinium, 3,4-dicarbamoylpyridinium, 3- or 4-N-methylcarbamoylpyridinium, 4-N,N-dimethylcarbamoylpyridinium, 4-N-ethylcarbamoylpyridinium, 3-N,N-diethylcarbamoylpyridinium, 4-N-propylcarbamoylpyridinium, 4-isopropylcarbamoylpyridinium and 4-hydroxymethylcarbamoylpyridinium, The functional groups present in compounds of the formula I, especially carboxyl and amino groups and also hydroxy and sulpho groups, are optionally protected by protecting groups that are used in penicillin, cephalosporin and peptide chemistry.

Protecting groups of this type can be split off easily, that is to say without undesired side reactions occurring, for example by solvolysis, reduction, photolysis or under physiological conditions.

Protecting groups of this type, and the way in which they are split off, are described, for example, in "Protective Groups in Organic Chemistry", Plenum Press, London, New York, 1973, in "The Peptides", Vol. 1, Schröder and Lübke, Academic Press, London, New York, 1965, and in "Methoden der organischen Chemie", Houben-Weyl, 4th edition, Vol. 15/1, Georg Thieme Verlag, Stuttgart, 1974.

Carboxyl groups are protected, for example, usually in esterified form, it being possible for such ester groups to be split off easily under mild conditions. Suitable protected carboxyl groups are, for example, lower alkoxycarbonyl, for example methoxycarbonyl or ethoxycarbonyl; especially tert.-lower alkoxycarbonyl, for example tert.-butoxycarbonyl; polycycloalkoxycarbonyl, for example adamantyloxycarbonyl; arylmethoxycarbonyl in which aryl preferably represents one or two phenyl radicals optionally mono-substituted or poly-substituted, for example, by lower alkyl, especially tert.-lower alkyl, for example tert.-butyl, by lower alkoxy, such as methoxy, by hydroxy, by halogen, for example chlorine, and/or by nitro, such as optionally substituted, for example as mentioned above, benzyloxycarbonyl, for example 4-nitrobenzyloxycarbonyl or 4-methoxybenzyloxycarbonyl or optionally substituted, for example as mentioned above, diphenylmethoxycarbonyl, for example diphenylmethoxycarbonyl or di-(4-methoxyphenyl)methoxycarbonyl; or 2-halo-lower alkoxycarbonyl, for example 2,2,2-trichloroethoxycarbonyl, 2-chloroethoxycarbonyl, 2-bromoethoxycarbonyl or 2-iodoethoxycarbonyl; 2-$(S_1)(S_2)(S_3)$-silylethoxycarbonyl, in which the substituents $S_1$, $S_2$ and $S_3$, independently of one another, each represents an optionally substituted, for example by lower alkyl, lower alkoxy, aryl, halogen or nitro, aliphatic, araliphatic, cycloaliphatic or aromatic hydrocarbon radical having, for example, up to 15 carbon atoms, such as a corresponding optionally substituted lower alkyl, aryl-lower alkyl, cycloalkyl or aryl radical, for example 2-tri-lower alkylsilylethoxycarbonyl, such as 2-trimethylsilylethoxycarbonyl or 2-(dibutylmethylsilyl)ethoxycarbonyl, or 2-triarylsilylethoxycarbonyl, such as 2-triphenylsilylethoxycarbonyl; or 1-lower alkoxy-lower alkoxycarbonyl, such as methoxymethoxycarbonyl, 1-methoxyethoxycarbonyl or 1-ethoxymethoxycarbonyl; or 1-lower alkylthio-lower alkoxycarbonyl, such as 1-methylthiomethoxycarbonyl or 1-ethylthioethoxycarbonyl; or aroylmethoxycarbonyl, in which the aroyl group preferably represents benzoyl optionally substituted, for example, by halogen, such as bromine, for example phenacyloxycarbonyl; or polyhaloaryloxycarbonyl, such as pentachlorophenoxycarbonyl. Esterified carboxyl groups are likewise corresponding silyloxycarbonyl, especially organic silyloxycarbonyl, groups or corresponding stannyloxycarbonyl groups. In these groups, the silicon or tin atom, respectively, preferably contains as substituents lower alkyl, especially methyl, lower alkoxy, for example methoxy, and/or halogen, for example chlorine. Suitable silyl- and stannyl-protecting groups are especially tri-lower alkylsilyl, especially trimethylsilyl, also dimethyl-tert.-butylsilyl, lower alkoxy-lower alkylhalosilyl, for example methoxymethylchlorosilyl, or di-lower alkylhalosilyl, for example dimethylchlorosilyl, or correspondingly substituted stannyl compounds, for example tri-n-butylstannyl.

Preferred protected carboxyl groups are tert.-butoxycarbonyl, benzyloxycarbonyl optionally substituted, for example, as mentioned, for example 4-nitrobenzyloxycarbonyl and diphenylmethoxycarbonyl.

An esterified carboxyl group that can be split under physiological conditions is especially an acyloxymethoxycarbonyl group, in which acyl represents, for example, the radical of an organic carboxylic acid, especially an optionally substituted lower alkanecarboxylic acid, or in which acyloxymethyl forms the radical of a lactone. Such groups are lower alkanoyloxymethoxycarbonyl, for example acetoxymethoxycarbonyl or pivaloyloxymethoxycarbonyl; amino-lower alkanoyloxymethoxycarbonyl, especially α-amino-lower alkanoyloxymethoxycarbonyl, for example glycyloxymethoxycarbonyl, L-valyloxymethoxycarbonyl or L-leucyloxymethoxycarbonyl; phthalidyloxycarbonyl, for example 2-phthalidyloxycarbonyl; or indanyloxycarbonyl, for example 5-indanyloxycarbonyl.

A protected amino group may be present, for example, in the form of an acylamino, monoarylmethylamino, diarylmethylamino, triarylmethylamino, etherified mercaptoamino, 1-acyl-2-lower alkylideneamino, silylamino, stannylamino or azido group that may readily be split off.

In a corresponding acylamino group, acyl is, for example, the acyl radical of an organic carboxylic acid having, for example, up to 18 carbon atoms, especially of an aliphatic carboxylic acid optionally substituted, for example, by halogen or aryl, or of an aromatic carboxylic acid optionally substituted, for example, by halogen, lower alkoxy or nitro, or of a carbonic acid semi-ester. Such acyl groups are, for example, lower alkanoyl, such as formyl, acetyl and propionyl; halo-lower alkanoyl, such as 2-haloacetyl, especially 2-chloroacetyl, 2-bromoacetyl, 2-iodoacetyl, 2,2-dichloroacetyl or 2,2,2-trichloroacetyl; phenacetyl; phenoxyacetyl; thienylacetyl; benzoyl; 4-chlorobenzoyl, 4-methoxybenzoyl or 4-nitrobenzoyl; lower alkoxycarbonyl, especially tert.-lower alkoxycarbonyl, for example tert.-butoxycarbonyl; polycycloalkoxycarbonyl, for example adamantyloxycarbonyl; arylmethoxycarbonyl in which aryl preferably represents one or two phenyl radicals optionally mono-substituted or poly-substituted, for example, by lower alkyl, especially tert.-lower alkyl, for example tert.-butyl, by lower alkoxy, such as methoxy, by hydroxy, by halogen, for example chlorine, and/or by nitro, such as optionally substituted benzyloxycarbonyl, for example 4-nitrobenzyloxycarbonyl, or substituted diphenylmethoxycarbonyl, for example benzhydryloxycarbonyl or di-(4-methoxyphenyl)methoxycarbonyl; or 2-halo-lower alkoxycarbonyl, for example 2,2,2-trichloroethoxycarbonyl, 2-chloroethoxycarbonyl, 2-bromoethoxycarbonyl or 2-iodoethoxycarbonyl; 2-($S_1$)($S_2$)($S_3$)-silylethoxycarbonyl, in which the substituents $S_1$, $S_2$ and $S_3$, independently of one another, each represents an aliphatic, araliphatic, cycloaliphatic or aromatic hydrocarbon radical having, for example, up to 15 carbon atoms optionally substituted, for example, by lower alkyl, lower alkoxy, aryl, halogen or nitro, such as a corresponding optionally substituted lower alkyl, aryl-lower alkyl, cycloalkyl or aryl radical, for example 2-tri-lower alkylsilylethoxycarbonyl, such as 2-trimethylsilylethoxycarbonyl or 2-(dibutylmethylsilyl)ethoxycarbonyl, or 2-triarylsilylethoxycarbonyl, such as 2-triphenylsilylethoxycarbonyl; or aroylmethoxycarbonyl, in which the aroyl group preferably represents benzoyl optionally substituted, for example, by halogen, such as bromine, for example phenacyloxycarbonyl.

Other acyl groups in acylamino groups are radicals of organic phosphoric, phosphonic or phosphinic acids of the formula $(R^1)(R^2)P(=O)—$, in which $R^1$ and $R^2$, independently of one another, each represents a hydroxy group etherified by a hydrocarbon radical or a hydrocarbon radical, wherein the hydrocarbon radicals preferably contain up to 15 carbon atoms, for example are of aliphatic, araliphatic, cycloaliphatic or aromatic nature, are optionally substituted, for example, by lower alkyl, lower alkoxy, aryl, halogen or nitro, and represent, for example, alkyl, especially lower alkyl, such as methyl, ethyl, propyl, isopropyl or butyl; phenyl-lower alkyl, such as benzyl, p-nitrobenzyl or p-chlorobenzyl; cycloalkyl, such as cyclopropyl, cyclopentyl, cyclohexyl or cycloheptyl; or homoaryl, such as phenyl, o-, m- or p-tolyl, p-methoxyphenyl, p-biphenylyl, p-chlorophenyl or p-nitrophenyl. Radicals of this type are, for example, dimethylphosphoryl, diethylphosphoryl, dipropylphosphoryl, diisopropylphosphoryl, dibenzylphosphoryl, di-p-nitrobenzylphosphoryl, dicyclohexylphosphoryl, diphenylphosphoryl, phenoxyphenylphosphonyl, diethylphosphinyl and diphenylphosphinyl.

In a mono-, di- or tri-arylmethylamino group, the aryl radicals are especially optionally substituted phenyl radicals. Groups of this type are, for example, benzylamino, diphenylmethylamino or tritylamino.

An etherified mercapto group in an amino group protected by such a radical is especially arylthio or aryl-lower alkylthio, in which aryl is especially phenyl optionally substituted, for example, by lower alkyl, such as methyl or tert.-butyl, by lower alkoxy, such as methoxy, by halogen, such as chlorine, and/or by nitro. A corresponding amino-protecting group is, for example, 4-nitrophenylthio.

In a 1-acyl-2-lower alkylidene radical that can be used as an amino-protecting group, acyl is preferably the corresponding radical of a lower alkanecarboxylic acid, of a benzoic acid optionally substituted, for example, by lower alkyl, such as methyl or tert.-butyl, by lower alkoxy, such as methoxy, by halogen, such as chlorine, and/or by nitro, or of a carbonic acid semi-ester, such as a carbonic acid lower alkyl semi-ester. Corresponding protecting groups are especially 1-lower alkanoyl-2-propylidene, for example 1-acetyl-2-propylidene, or 1-lower alkoxycarbonyl-2-propylidene, for example 1-ethoxycarbonyl-2-propylidene.

A silylamino or stannylamino group is especially an organic silylamino or stannylamino group in which the silicon or tin atom, respectively, preferably contains lower alkyl, especially methyl, lower alkoxy, for example methoxy, and/or halogen, for example chlorine, as substituents. Corresponding silyl or stannyl groups are especially trilower alkylsilyl, especially trimethylsilyl and also dimethyl-tert.-butylsilyl; lower alkoxy-lower alkylhalosilyl, for example methoxymethylchlorosilyl; or di-lower alkyl halosilyl, for example dimethylchlorosilyl; or correspondingly substituted stannyl, for example tri-n-butylstannyl.

An amino group may alternatively be protected in protonated form; suitable anions are especially those of strong inorganic acids, such as those of hydrohalic acids, for example the chlorine or bromine anion, or those of sulphonic acid, such as p-toluenesulphonic acid.

Preferred amino-protecting groups are the acyl radicals of carbonic acid semi-esters, especially tert.-butoxycarbonyl, diphenylmethoxycarbonyl or benzyloxycarbonyl optionally substituted, for example as stated, or 2-halo-lower alkoxycarbonyl, such as 2,2,2-trichloroethoxycarbonyl.

Hydroxy-protecting groups are, for example, acyl radicals, such as 2,2-dichloroacetyl; or especially the acyl radicals of carbonic acic semi-esters mentioned in connection with a protected amino group, especially 2,2,2-trichloroethoxycarbonyl; or organic silyl or stannyl radicals; also 2-oxa-aliphatic, 2-oxacycloaliphatic, 2-thiaaliphatic, or 2-thiacycloaliphatic hydrocarbon radicals that can readily be split off, especially 1-lower alkoxylower alkyl or 1-lower alkylthio-lower alkyl, for example methoxymethyl, 1-methoxyethyl, 1-ethoxyethyl, 1-methylthiomethyl, 1-methylthioethyl or 1-ethylthioethyl; or 2-oxacyclo-lower alkyl or 2-thiacyclo-lower alkyl having 5–7 ring atoms, for example 2-tetrahydrofuryl or 2-tetrahydropyranyl; or corresponding thia-analogues; and optionally substituted α-phenyl-lower alkyl radicals that can readily be split off, such as optionally substituted benzyl or diphenylmethyl, suitable substituents of the phenyl radicals being, for example, halogen, such as chlorine, lower alkoxy, such as methoxy, and/or nitro.

A protected sulpho group is especially a sulpho group esterified by an aliphatic, cycloaliphatic, cycloaliphatic-aliphatic, aromatic or araliphatic alcohol, such as a lower alkanol, or by a silyl or stannyl radical, such as trilower alkylsilyl. In a sulpho group the hydroxy group may be etherified, for example, in the same manner as the hydroxy group in an esterified carboxy group.

Salts are especially those of compounds of the formula I with acidic groups, for example with free carboxyl and sulpho groups. Salts of this type are especially metal or ammonium salts, such as alkali metal and alkaline earth metal salts, for example sodium, potassium, magnesium or calcium salts, and ammonium salts with ammonia or suitable organic amines, wherein especially aliphatic, cycloaliphatic, cycloaliphatic-aliphatic or araliphatic primary, secondary or tertiary mono-, di- or polyamines and heterocyclic bases are suitable for the salt formation, such as lower alkylamines, for example triethylamine; hydroxy-lower alkylamines, for example 2-hydroxyethylamine, bis-(2-hydroxyethyl)amine or tris-(2-hydroxyethyl)amine; basic aliphatic esters of carboxylic acids, for example 4-aminobenzoic acid 2-diethylaminoethyl ester; lower alkylene amines, for example 1-ethylpiperidine; cycloalkylamines, for example dicyclohexylamine; or benzylamines; for example N,N'-dibenzylethylenediamine; and also bases of the pyridine type, for example pyridine, collidine or quinoline. Compounds of the formula I with a basic group can form acid addition salts, for example with inorganic acids, such as hydrochloric acid, sulphuric acid or phosphoric acid, or with suitable organic carboxylic or sulphonic acids, for example trifluoroacetic acid, and with amino acids, such as arginine and lysine. If several acidic or basic groups are present, mono-salts or poly-salts may be formed. Compounds of the formula I with a free carboxyl group and a free amino group may also be present in the form of inner salts, that is to say in zwitter-ion form, or a part of the molecule, for example the terminal aminocarboxylic acid function, may be present in the form of an inner salt and another part, for example the 4-carboxyl group, in the form of a normal salt.

It is also possible to use pharmaceutically unsuitable salts for isolation or purification. For therapeutic use, only pharmaceutically tolerable salts are possible, and these are therefore preferred.

The acyl radical of the 7β-amino group contains one, or optionally two, asymmetric centres. The asymmetric centre optionally present in A, that is to say when A is methylene substituted by amino, hydroxy, carboxyl or sulpho, is in the R,S-configuration or preferably the R-configuration. The asymmetric centre of the terminal aminocarboxylic acid grouping may have a R-, a S- or a R,S-configuration, the R-configuration being preferred.

The group =N—O—R⁰ may be in the syn- or anti-form, the syn-form being preferred.

The substituted aminothiazolyl group of the partial formula

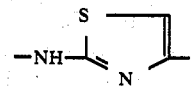

may also be present in tautomeric form as an iminothiazolinyl group of the partial formula

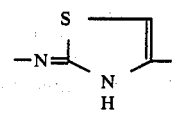

or as a mixture of both forms. The balance between the two tautomers depends on the nature of the substituents and external factors, such as temperature, solvent or pH value. Within the scope of the present invention, this group is referred to in the description and in the claims only as "aminothiazolyl", although the iminothiazolinyl form is also to be included.

The compounds of the formula I in which carboxyl groups are optionally esterified in a form that can be split under physiological conditions, and their pharmaceutically acceptable, non-toxic salts are valuable antibiotically active substances that in particular can be used as anti-bacterial antibiotics. For example, they are effective in vitro against gram-positive and gram-negative microorganisms, such as against cocci, for example staphylococci, streptococci and micrococci, including types of neisseria, in minimal concentrations of approximately 0.05 mcg/ml to approximately 32 mcg/ml, and against enterobacteriaceae, for example against Haemophilus, in minimal concentrations of approximately 0.5 mcg/ml to 128 mcg/ml. In vivo on subcutaneous administration to a mouse, they are effective, for example, against gram-positive causative agents (in the case of acute infection in minimal doses of approximately 10 to 30 mg/kg) and against gram-negative causative agents (in the case of acute infection in minimal doses of approximately 0.8–100 mg/kg), and especially against enterobacteria, including β-lactamase-forming enterobacteria, for example against *Proteus morganii* and *Proteus mirabilis* (in the case of acute infections ED₅₀ 8 mg/kg). The new compounds can therefore be used correspondingly, for example in the form of antibiotically active preparations, for the treatment of infections caused by gram-positive or gram-negative bacteria and cocci, especially of infections caused by enterobacteria, such as *Proteus morganii* and *Proteus mirabilis*.

Compounds of the formula I in which the functional groups are protected are used as starting materials for the manufacture of compounds of the formula I.

The present invention relates especially to those compounds of the formula I in which
the —($C_nH_{2n}$)— group is unbranched,
n has the meaning given,
X represents oxygen, sulphur or —NH—,
Y represents oxygen,
A represents methylene, aminomethylene, hydroxymethylene, carboxymethylene, sulphomethylene, hydroxyiminomethylene or methoxyiminomethylene,
$R_1$ represents hydrogen, lower alkyl, lower alkoxy, halogen or a group of the formula —$CH_2$—$R_2$, in which $R_2$ represents lower alkanoyloxy, carbamoyloxy, N-lower alkylcarbamoyloxy, triazolylthio, tetrazolylthio, thiazolylthio, thiatriazolylthio, thiadiazolylthio, oxazolylthio, oxadiazolylthio or pyridinium, wherein the heterocyclic rings may optionally be substituted, for example, by lower alkyl, N,N-di-lower alkylamino-lower alkyl, carboxylower alkyl, sulpho-lower alkyl, amino, carboxy-lower alkanoylamino or carbamoyl, and represents hydrogen or methoxy, $R_3$ represents hydrogen or methoxy, pharmaceutically acceptable salts of such compounds and the starting materials and intermediates that can be used for their manufacture.

Attention is drawn in particular to compounds of the formula I in which the $-(C_nH_{2n})-$ group is unbranched and n has the meaning given, X represents oxygen, sulphur or $-NH-$, Y represents oxygen, A represents methylene, aminomethylene, hydroxymethylene or methoxyiminomethylene, $R_1$ represents hydrogen, methyl, methoxy, chlorine or a group of the formula $-CH_2-R_2$ in which $R_2$ represents acetoxy, carbamoyloxy, tetrazolylthio, especially 1-methyl-1H-tetrazol-5-ylthio, 1-sulphomethyl-1H-tetrazol-5-ylthio, 1-carboxymethyl-1H-tetrazol-5-ylthio or 1-(2-dimethylaminoethyl)-1H-tetrazol-5-ylthio, or thiadiazolylthio, especially 2-methyl-1,3,4-thiadiazol-5-ylthio, or carbamoylpyridinium, especially 4-carbamoylpyridinium, and $R_3$ represents hydrogen, pharmaceutically acceptable salts of such compounds and the starting materials and intermediates that can be used for their manufacture.

The invention relates especially to the compounds of the formula I described in the Examples, their pharmaceutically tolerable salts, and the starting materials and intermediates described therein.

The compounds of the present invention are produced in accordance with processes that are known per se.

Compounds of the formula I in which the carboxyl groups are optionally esterified in a form that can be split under physiological conditions, and the salts thereof, are produced by liberating, in a starting compound of the formula I in which at least one of the functional groups present is protected, the functional group or groups, if desired converting a radical $R_1$ in a resulting compound into a different radical $R_1$ and/or, if desired, converting a free carboxyl group into an esterified carboxyl group that can be split under physiological conditions and/or, if desired, separating a resulting isomeric mixture into the individual isomers and/or, if desired, converting a resulting compound into a salt or a resulting salt into a free compound or into a different salt.

In the starting compounds of the formula I in which functional groups are protected, these, for example protected carboxyl, amino, hydroxy, mercapto and/or sulpho groups, are optionally liberated in stages or simultaneously in a manner known per se, such as by means of solvolysis, especially hydrolysis, alcoholysis or acidolysis, or by means of reduction, especially hydrogenolysis or chemical reduction.

For example, a lower alkoxycarbonyl group optionally substituted in the 2-position by a silyl group or in the 1-position by lower alkoxy or lower alkylthio, a polycycloalkoxycarbonyl group or a diphenylmethoxycarbonyl group, may be converted into the free carboxyl group by treating with a suitable acidic agent, such as formic acid or trifluoroacetic acid, optionally with the addition of a nucleophilic compound, such as phenol or anisole. An optionally substituted benzyloxycarbonyl group can be liberated, for example, by means of hydrogenolysis by treating with hydrogen in the presence of a hydrogenating catalyst, such as a palladium catalyst. Further, benzyloxycarbonyl groups containing certain substituents, such as 4-nitrobenzyloxycarbonyl, can be converted into free carboxyl groups also by means of chemical reduction, for example by treating with an alkali metal dithionite, for example sodium dithionite, or with a reducing metal, for example zinc, or a metal salt, such as a chromium(II) salt, for example chromium(II) chloride, usually in the presence of a hydrogen-yielding agent that together with the metal can bring about the production of nascent hydrogen, such as an acid, especially a carboxylic acid or α-hydroxycarboxylic acid, such as especially acetic acid, formic acid, glycolic acid, diphenylglycolic acid, lactic acid, mandelic acid, p-chloromandelic acid, tartaric acid and the like, or in the presence of an alcohol or thiol, water preferably being added. By treating with a reducing metal or metal salt as described above, it is also possible to convert a 2-halo-lower alkoxycarbonyl group (optionally after conversion of a 2-bromo-lower alkoxycarbonyl group into a 2-iodo-lower alkoxycarbonyl group) or an aroylmethoxycarbonyl group into the free carboxyl group, wherein an aroylmethoxycarbonyl group can likewise be split by treating with a nucleophilic, preferably salt-forming, reagent, such as sodium thiophenolate or sodium iodide. A substituted silylethoxycarbonyl group can also be converted into the free carboxyl group by treating with a salt of hydrofluoroic acid that yields fluoride anions, such as an alkali metal fluoride, for example sodium or potassium fluoride, in the presence of a macrocyclic polyether ("crown ether"), or with a fluoride of an organic quaternary base, such as a tetraalkylammonium fluoride or trialkylarylammonium fluoride, for example tetraethylammonium fluoride or tetrabutylammonium fluoride, in the presence of an aprotic polar solvent, such as dimethyl sulphoxide or N,N-dimethylacetamide. A polyhaloaryloxycarbonyl group, such as the pentachlorophenoxycarbonyl group, is hydrolysed to form the free carboxyl group under mild basic conditions, such as by dilute sodium hydroxide solution or organic bases in the presence of water.

A carboxyl group protected, for example, by silylation or stannylation, can be liberated in the usual manner, for example by treating with water or an alcohol.

A protected amino group is liberated in a manner known per se and, depending on the nature of the protecting group, in a variety of ways, for example by means of solvolysis or reduction. A 2-halo-lower alkoxycarbonylamino group (optionally after conversion of a 2-bromo-lower alkoxycarbonyl group into a 2-iodo-lower alkoxycarbonyl group), an acylmethoxycarbonylamino group or a 4-nitrobenzyloxycarbonylamino group can be liberated, for example, by treating with a suitable chemical reducing agent, such as zinc in the presence of a carboxylic or α-hydroxycarboxylic acid, such as aqueous acetic acid; an aroylmethoxycarbonylamino group can be liberated by treating with a nucleophilic, preferably salt-forming, reagent, such as sodium thiophenolate, and a 4-nitrobenzyloxycarbonylamino group by treating with an alkali metal dithionite, for example sodium dithionite; a diphenylmethoxycarbonylamino, tert.-lower alkoxycarbonylamino, 2-$(S_1)(S_2)(S_3)$silylethoxycarbonylamino or polycycloalkoxycarbonylamino group can be liberated by treating, for example, with formic or trifluoroacetic acid; an optionally substituted benzyloxycarbonylamino group can be liberated, for example, by means of hydrogenolysis by treating with hydrogen in the presence of a hydrogenating catalyst, such as a palladium catalyst; a triarylmethyl group can be liberated, for example, by treating with aqueous mineral acid, and an amino group protected by an organic silyl or stannyl group can be liberated, for example by means of hydrolysis or alcoholysis. An amino group protected by 2-haloacetyl, such as 2-chloroacetyl, can be liberated by treating with thiourea in the presence of a base, or with a thiolate salt, such as an alkali metal thiolate of the thiourea, and subsequent solvolysis, such as alcoholysis or hydrolysis, of the resulting condensation product. An amino group protected by a substituted silylethoxycarbonyl group can also be converted into the free amino group by treating with a salt of hydrofluoric acid that yields fluoride anions, as specified above for the liberation of a correspondingly protected carboxyl group. A phosphoramido, phosphonamido or phosphinamido group can be converted into the free amino group by treating with a phosphorus-containing acid, such as a phosphoric, phosphonic or phosphinic acid, for example orthophosphoric acid or polyphosphoric acid, with an acidic ester thereof, for example monomethyl, monoethyl, dimethyl or diethyl phosphate or monomethylphosphonic acid, or an anhydride thereof, such as phosphorus pentoxide, and the like.

An amino group protected in the form of an azido group is converted into the free amino group in a manner known per se by reduction, for example by catalytic hydrogenation with hydrogen and a hydrogenating catalyst, such as platinum oxide, palladium, or alternatively Raney nickel, or by zinc and acid, such as acetic acid. The catalytic hydrogenation is preferably carried out in an inert solvent, such as a halogenated hydrocarbon, for example methylene chloride, or in water or a mixture of water and an organic solvent, such as an alcohol or dioxan, at approximately 20° to 25°, or at a reduced or elevated temperature.

A hydroxy group protected by an acyl group, a silyl or a stannyl group or by an optionally substituted α-phenyllower alkyl radical is liberated like a correspondingly protected amino group. A hydroxy group protected by 2,2-dichloroacetyl is liberated by basic hydrolysis, and a hydroxy group protected by a 2-oxa-aliphatic, 2-oxacycloaliphatic, 2-thia-aliphatic or 2-thiacycloaliphatic hydrocarbon radical is liberated by acidolysis.

A protected sulpho group is liberated analogously to a protected carboxyl group.

Preferably the protecting groups are so selected that they can all be split off simultaneously, for example by acidolysis, such as by treating with trifluoroacetic acid or formic acid, or by reduction, such as by treating with zinc and glacial acetic acid, or with hydrogen and a hydrogenating catalyst, such as a palladium/carbon catalyst.

The described splitting reactions are carried out under conditions that are known per se, if necessary while cooling or heating, in a closed vessel and/or in an inert gas atmosphere, for example a nitrogen atmosphere.

In a compound of the formula I in which an amino group is, if necessary, protected, and in which the carboxyl group in the 4-position of the cephem ring is present in free form, an $R_1$ group can be replaced by a different $R_1$ radical or be converted into a different $R_1$ radical in a manner known per se. For example, it is possible in a compound of the formula I in which $R_1$ represents a group of the formula $-CH_2-R_2$, and $R_2$ represents, for example, a radical that can be replaced by nucleophilic substituents, or in a salt of such a compound, to replace such a radical $R_2$ by an etherified or esterified mercapto group $R_2$ by treating with a corresponding mercaptan compound or with a thiocarboxylic acid compound. A suitable radical that can be replaced by an etherified mercapto group is, for example, a hydroxy group esterified by a lower aliphatic carboxylic acid. Esterified hydroxy groups of this type are especially acetoxy, and also formyloxy.

The reaction of such a compound with a suitable mercaptan compound can be carried out under neutral or slightly basic conditions in the presence of water and optionally a water-miscible organic solvent. The basic conditions may be established, for example, by adding an inorganic base, such as an alkali metal or alkaline earth metal hydroxide, carbonate or bicarbonate, for example sodium, potassium or calcium hydroxide, carbonate or bicarbonate. Suitable organic solvents are, for example, water-miscible alcohols, such as lower alkanols, such as methanol or ethanol, ketones, for example lower alkanones, such as acetone, amides, for example lower alkanecarboxylic acid amides, such as dimethylformamide, or nitriles, for example lower alkanecarboxylic acid nitriles, such as acetonitrile, and the like.

Esterified hydroxy groups $R_2$ in a compound of the formula I in which $R_1$ represents the group $-CH_2-R_2$, wherein $R_2$ is a hydroxy group esterified by the acyl radical of an optionally substituted semi-amide of carbonic acid, can be introduced, for example, by reacting a corresponding compound of the formula I, in which $R_2$ represents free hydroxy (which can be liberated, for example, by splitting off the acetyl radical from an acetoxy group $R_2$, for example by means of hydrolysis in a slightly basic medium, such as with an aqueous sodium hydroxide solution at a pH of 9–10, or by treating with a suitable esterase, such as a corresponding enzyme from *Rhizobium tritolii, Rhizobium lupinii, Rhizobium japonicum* or *Bacillus subtilis,* or with a suitable citrous esterase, for example from orange peel), with a suitable carbonic acid derivative, especially with an isocyanate compound or carbamic acid compound, such as a silyl isocyanate, for example silyl tetraisocyanate, a sulphonyl isocyanate, for example chlorosulphonyl isocyanate, or carbamic acid halide, for example carbamic acid chloride (which result in N-unsubstituted 3-aminocarbonyloxymethyl compounds), or with a N-substituted isocyanate compound or with a N-monosubstituted or N,N-disubstituted carbamic acid compound, such as a corresponding carbamic acid halide, for example a carbamic acid chloride, the reaction usually being carried out in the presence of a solvent or diluent and, if necessary while cooling or heating, in a closed vessel and/or in an inert gas atmosphere, for example a nitrogen atmosphere.

Also, a compound of the formula I in which $R_1$ represents a $-CH_2-R_2$ group, wherein $R_2$ is, for example, the above-defined radical that can be replaced by nucleophilic substitution, can be reacted with a tertiary organic base, especially an optionally substituted pyridine, under neutral or slightly acidic conditions, preferably at a pH value of approximately 6.5, in the presence of water and optionally in a water-miscible organic solvent, and compounds of the formula I can thus be obtained in which $R_1$ represents the radical of the formula $-CH_2-R_2$ and $R_2$ represents a quaternary ammonium group. The slightly acidic conditions can be established by adding a suitable organic or inorganic acid, for example acetic acid, hydrochloric acid, phosphoric acid or alternatively sulphuric acid. Suitable organic solvents are, for example, the water-miscible solvents mentioned hereinbefore. To increase the yield, certain salts can be added to the reaction mixture, for example alkali metal salts, such as sodium and especially potassium salts, of inorganic acids, such as hydrohalic acids, for example hydrochloric and especially hydriodic acid, and thiocyanic acid, or of organic acids, such as lower alkanecarboxylic acids, for example acetic acid. Examples of such salts are potassium iodide and potassium thiocyanate. It is also possible to use salts of suitable anion exchangers, for example liquid ion exchangers in salt form, such as, for example, Amberlites LA-1 (liquid secondary amines having a molecular weight of 351–393; oil-soluble and water-insoluble; meq/g=2-.5–2.7, for example in acetate form), with acids, for example acetic acid, for this purpose.

Quaternary ammonium groups $R_2$ may advantageously be produced using an intermediate of the formula I in which $R_2$ represents a substituted, especially an aromatically substituted, carbonylthio group, and more especially a benzoylthio group. Such an intermediate, which can be obtained, for example, by reacting a compound of the formula I, in which $R_2$ in the radical $R_1$ represents an esterified hydroxy group, especially a lower alkanoyloxy group, for example an acetoxy group, with a suitable salt, such as an alkali metal salt, for example a sodium salt, of a thiocarboxylic acid, such as an aromatic thiocarboxylic acid, for example thiobenzoic acid, is reacted with a tertiary amine, especially a tertiary heterocyclic base, such as an optionally substituted pyridine, thus producing the quaternary ammonium compound. The reaction is usually carried out in the presence of a suitable desulphurising agent, especially a mercury salt, for example mercury(II) perchlorate, and of a suitable solvent or diluent or a mixture thereof, if necessary while cooling or heating, in a closed vessel and/or in an inert gas atmosphere, for example a nitrogen atmosphere.

The conversion of a free carboxyl group in a resulting compound of the formula I into an esterified carboxyl group that can be split under physiological conditions is carried out according to esterifying methods that are known per se, for example by esterifying a compound of the formula I, in which other functional groups, such as amino, hydroxy or sulpho groups, are optionally present in protected form, or a functional derivative thereof reactive with respect to the carboxyl group to be esterified, or a salt thereof, with a corresponding alcohol or a reactive functional derivative thereof.

Salts of compounds of the formula I can be produced in a manner known per se. For example, it is possible to form salts of compounds of the formula I having acidic groups, for example by treating with metal compounds, such as alkali metal salts of suitable carboxylic acids, for example the sodium salt of α-ethylcaproic acid, or sodium bicarbonate, or with ammonia or a suitable organic amine, wherein preferably stoichiometric amounts or only a slight excess of the salt-forming agent is used. Acid addition salts of compounds of the formula I are obtained in the usual manner, for example by treating with an acid or a suitable anion exchange reagent. Inner salts of compounds of the formula I that contain a free carboxyl group can be formed, for example, by neutralising salts, such as acid addition salts, to the isoelectric point, for example with weak bases, or by treating with liquid ion exchangers.

Salts can be converted into the free compounsds in the usual manner, for example, metal and ammonium salts can be converted by treating with suitable acids, and acid addition salts by treating with a suitable basic agent.

The process includes also those embodiments according to which compounds produced as intermediates are used as starting materials and the remaining process steps are carried out with these, or the process is interrupted at any stage; furthermore, it is possible to use starting materials in the form of derivatives or the starting materials can be formed during the reaction.

Preferably, the starting materials and reaction conditions are so selected that the compounds stated hereinbefore as being especially preferred are obtained.

The invention also relates to starting compounds of the formula I in which at least one of the functional groups is present in protected form and to processes for their manufacture. These compounds may be produced in a manner known per se, for example (a) by acylating the amino group in a compound of the formula

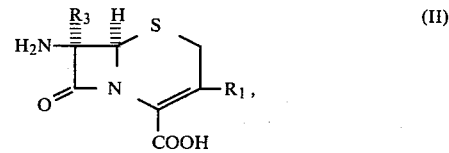

in which the amino group is optionally substituted by a group allowing acylation and in which the 4-carboxyl group and optionally other functional groups present in the radical $R_1$ may be in protected form, by treating with an acylating agent introducing the acyl radical of a carboxylic acid of the formula

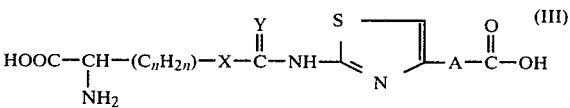

in which the aminocarboxylic acid grouping HOOC—CH(NH$_2$)— and optionally other functional groups present in the grouping A are in protected form, or (b) by acylating the amino group in a compound of the formula

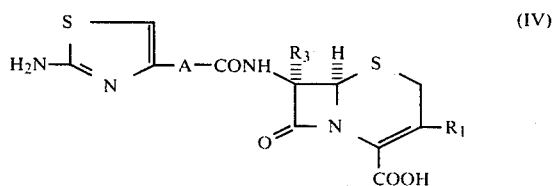

in which the amino group is optionally substituted by a group allowing acylation and in which the 4-carboxyl group and optionally other functional groups present in the radical R₁ and in the grouping A may be in protected form, by treating with an acylating agent introducing the corresponding acyl radical of a carboxylic acid of the formula

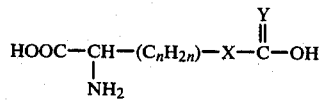 (V)

in which the aminocarboxylic acid grouping HOOC—CH(NH₂)— is present in protected form, or (c) by acylating the —X—H group in a compound of the formula

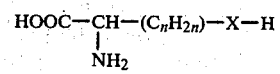 (VI)

in which X represents oxygen, sulphur or an —NH— group and in which the aminocarboxylic acid grouping HOOC—CH(NH₂)— is present in protected form, with an acylating agent introducing the corresponding acyl radical of a carboxylic acid of the formula

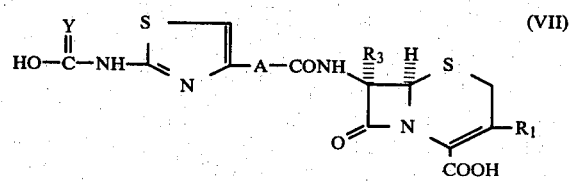 (VII)

in which the 4-carboxyl group and optionally other functional groups present in the radical R₁ and in the grouping A may be in protected form, or (d) by condensing a compound of the formula

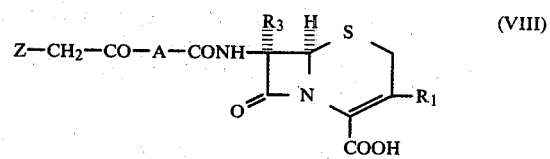 (VIII)

in which Z represents a halogen atom and in which functional groups are optionally protected, or a salt thereof, with a thiourea of the formula

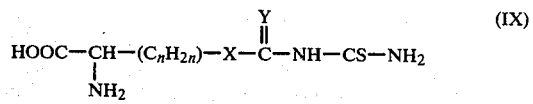 (IX)

in which functional groups are protected, or with a salt thereof, or (e) for the manufacture of compounds of the formula I in which R₁ is hydrogen, by replacing by hydrogen the R₁ᵃ group in a compound of the formula

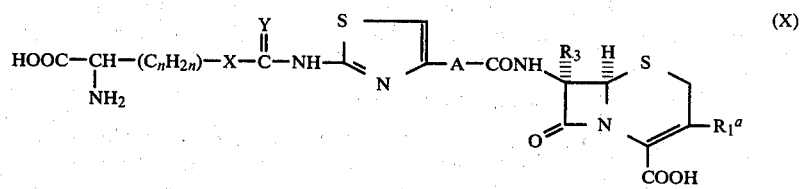 (X)

in which R₁ᵃ represents an optionally esterified hydroxy group or a secondary or tertiary amino group and R₃ represents hydrogen, and in which functional groups are optionally protected, or (f) for the manufacture of compounds of the formula I in which R₁ is hydrogen and in which functional groups are protected, by cyclising a compound of the formula

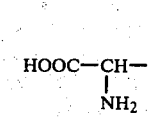
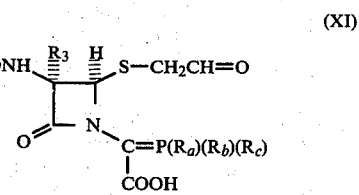 (XI)

in which R₃ represents hydrogen and each of th radicals Rₐ, R_b and R_c represents an optionally substituted hydrocarbon radical, and in which functional groups are protected, O=P(Rₐ)(R_b)(R_c) being split off, or (g) for the manufacture of compounds of the formula I in which R₁ represents lower alkyl, an esterified or etherified hydroxy group or halogen, and in which functional groups are protected, by cyclising a compound of the formula

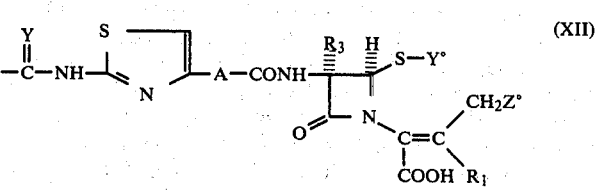 (XII)

in which $R_1$ has the meaning given above, $R_3$ represents hydrogen, $Y^o$ represents a leaving group and $Z^o$ represents hydrogen or halogen, and in which functional groups are protected, $Y^o$ and $Z^o$ being split off, or (h) by isomerising a 2-cephem compound of the formula

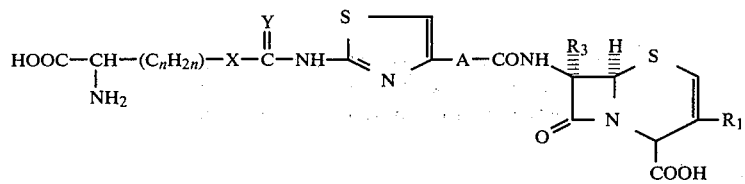
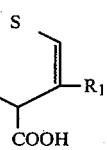

(XIII)

in which functional groups are protected, to form the corresponding 3-cephem compound of the formula I, and, if desired, protecting still unprotected functional groups in a resulting compound or exchanging one protecting group for another, and/or, if desired, converting a radical A or R, into a different radical A or $R_1$, respectively, and/or, if desired, converting a resulting compound in which $R_3$ represents hydrogen into a compound in which $R_3$ represents methoxy and/or, if desired, converting a resulting compound into a salt or a resulting salt into a free compound or into a different salt.

Processes (a), (b) and (c) (Acylation)

Radicals optionally present in a starting material of the formula II or IV that substitute the amino group and allow its acylation are, for example, organic silyl or stannyl groups, or also ylidene groups that together with the amino group form a Schiff's base. The said organic silyl or stannyl groups are, for example, the same as those that also are able to form a protected carboxyl group with the 4-carboxyl group at the cephem ring. In the silylation or stannylation of a carboxyl group in a starting material of the formula II or IV, by using an excess of silylation or stannylation agent the amino group can likewise be silylated or stannylated.

The mentioned ylidene groups are especially arylmethylene groups, in which aryl is especially a carbocyclic, especially monocyclic, aryl radical, for example phenyl optionally substituted, for example, by nitro or hydroxy.

The other functional groups present in the starting materials of the formulae II to VII may be protected by the protecting groups already mentioned under the compounds of the formula I. Preferably all reactive functional groups that do not participate in the acylation reaction, but especially acylatable amino, hydroxy and mercapto groups optionally present, are protected.

Acylating agents introducing the acyl radical of a carboxylic acid of the formula III or V are, for example, the carboxylic acid itself or reactive functional derivatives thereof.

If a free acid of the formula III or V in which all functional groups apart from the reacting carboxyl group are protected is used as acylating agent, suitable condensation agents are usually used, such as carbodiimides, for example N,N'-diethylcarbodiimide, N,N'-dipropylcarbodiimide, N,N'-dicyclohexylcarbodiimide or N-ethyl-N'-3-dimethylaminopropylcarbodiimide; suitable carbonyl compounds, for example carbonyldiimidazole; or isoxazolinium salts, for example N-ethyl-5-phenylisoxazolinium-3'-sulphonate and N-tert.-butyl-5-methylisoxazolinium perchlorate; or an acylamino compound, for example 2-ethoxyl-1-ethoxycarbonyl-1,2-dihydroquinoline.

The condensation reaction is preferably carried out in an anhydrous reaction medium, preferably in the presence of a solvent or diluent, for example methylene chloride, dimethylformamide, acetonitrile or tetrahydrofuran, if desired or necessary while cooling or heating and/or in an inert gas atmosphere.

A reactive, that is to say amide-forming, or ester-forming, functional derivative of an acid of the formula III, V or VII in which all the functional groups apart from the reacting acid group, are, or may be, protected is especially an anhydride of such an acid, including and preferably a mixed anhydride, but alternatively an inner anhydride, that is a corresponding ketene, or in the acid V, where X is the —NH— group, a corresponding isocyanate or isothiocyanate. Mixed anhydrides are, for example, those with inorganic acids, such as hydrohalic acids, that is the corresponding acid halides, for example the chlorides or bromides; or with hydrazoic acid, that is the corresponding acid azides; with a phosphorus-containing acid, for example phosphoric or phosphorous acid; or with a sulphur-containing acid, for example sulphuric acid; or with hydrocyanic acid. Other mixed anhydrides are, for example, those with organic carboxylic acids, such as with lower alkanecarboxylic acids optionally substituted, for example by halogen, such as fluorine or chlorine, for example pivalic acid or trichloroacetic acid; or with semi-esters, especially lower alkyl semi-esters of carbonic acid, such as the ethyl or isobutyl semi-ester of carbonic acid; or with organic, especially aliphatic or aromatic, sulphonic acids, for example p-toluenesulphonic acid. When A is hydroxymethylene, it is also possible to use a mixed inner anhydride of the acid III with the carbonic acid semi-ester of the α-hydroxy group.

Other acid derivatives of an acid of the formula III, V or VII, in which all functional groups apart from the reacting carbonyl group are, or may be, protected, that are suitable for the reaction with the amino, hydroxy or mercapto group are activated esters, such as esters with vinylogous alcohols (that is, enols), such as vinylogous lower alkenols; or iminiomethyl ester halides, such as dimethyliminiomethyl ester chloride (produced from carboxylic acid and dimethylchloromethylideneiminium chloride of the formula $[(CH_3)_2N=CHCl]^{\oplus}Cl^{\ominus}$; or aryl esters, such as 4-nitrophenyl ester or 2,3-dinitrophenyl ester; heteroaromatic esters such as benztriazolyl esters, for example 1-benztriazolyl ester; or diacylimino esters, such as succinylimino or phthalylimino ester.

The acylation with an acid derivative, such as an anhydride or, especially, with an acid halide, is preferably carried out in the presence of an acid-binding agent, for example an organic base, such as an organic amine, for example a tertiary amine, such as a tri-lower alkylamine, for example trimethylamine, triethylamine or ethyldiisopropylamine, or an N,N-di-lower alkylaniline, for example N,N-dimethylaniline, or a cyclic tertiary amine, such as an N-lower alkylated morpholine, such as N-methylmorpholine; or a base of the pyridine type, for example pyridine; an inorganic base, for example an alkali metal or alkaline earth metal hydroxide, carbonate or bicarbonate, for example sodium, potassium or calcium hydroxide, carbonate or bicarbonate; or an oxirane, for example a lower 1,2-alkylene oxide, such as ethylene oxide or propylene oxide.

The above acylation processes are preferably carried out in an inert, preferably anhydrous, solvent or solvent mixture, for example in a carboxylic acid amide, such as a formamide, for example dimethylformamide; in a halogenated hydrocarbon, for example methylene chloride, carbon tetrachloride or chlorobenzene; in a ketone, for example acetone; in an ester, for example ethyl acetate; or in a nitrile, for example acetonitrile; or mixtures thereof. The processes are carried out at room temperature, or if necessary reduced or elevated temperature, at approximately $-40°$ to approximately $100°$, preferably $-10°$ to $40°$, and/or in an inert gas atmosphere, for example a nitrogen atmosphere.

The acylation can also be carried out in the presence of an acylase producing the desired amide bond. Such acylases are known and are formed by a series of microorganisms, for example by acetobacter, such as *Acetobacter aurantium*, archromobacter, such as *Archromobacter aeris*, aeromonas, such as *Aeromonas hydrophila*, or *Bacillus megaterium*, for example 400. In particular amides, esters or thioesters, such as corresponding lower alkyl esters, for example the methyl or ethyl ester, of the carboxylic acid of the formula III are used in the enzymatic acylation. The enzymatic acylation is carried out in a nutrient medium containing the microorganism, in a filtrate of the culture liquor or, optionally after isolating the acylase, including after adsorption on a carrier, in an aqueous medium optionally containing a buffer, at approximately $30°-40°$, preferably at approximately $37°$.

In an acylating acid of the formula III, V or VII or in an acid derivative thereof, a protected amino group may alternatively be present in ionic form, that is to say the starting material of the formula III, V or VII may be used in the form of an acid addition salt, preferably with a strong inorganic acid, such as a hydrohalic acid, for example hydrochloric acid, or sulphuric acid.

An acid derivative can, if desired, be formed in situ. For example, a mixed anhydride is obtained by treating an acid of the formula III, or an acid of the formula V, in which X represents the direct bond, with correspondingly protected functional groups, or a suitable salt thereof, such as an ammonium salt, for example with an organic amine, such as 4-methylmorpholine, or a metal, for example an alkali metal, salt, with a suitable acid derivative such as a corresponding acid halide of an optionally substituted lower alkanecarboxylic acid, for example trichloroacetyl chloride, or with a semi-ester of a carbonic acid semi-halide, for example chloroformic acid ethyl ester or isobutyl ester, and the mixed anhydride obtained in this manner is used without isolation.

An acid chloride of an acid of the formula V, in which X represents oxygen, sulphur or an —NH— group and in which the aminocarboxylic acid grouping HOOC—CH(NH$_2$)— is present in protected form, may be formed, for example in situ, by treating an aminocarboxylic acid of the formula VI, in which X represents oxygen, sulphur or an —NH— group and the grouping HOOC—CH(NH$_2$)— is present in protected form, with phosgene in the presence of a hydrochloric acid acceptor in an inert organic solvent or solvent mixture. The hydrochloric acid acceptors, solvents and reaction conditions are the same as those mentioned for the acylation of compounds of the formula II or IV; for example, the reaction can be carried out in the presence of pyridine in methylene chloride and toluene at approximately 0° to approximately 10°.

In the same manner an acid chloride of an acid of the formula VII in which the 4-carboxyl group and other functional groups optionally present in the groups —A— and R$_1$ are protected, can be produced, for example in situ, from a correspondingly protected compound of the formula IV by treating with chlorosulphonyl isocyanate.

Process (d) (condensation)

In a starting compound of the formula VIII, Z is halogen, especially chlorine but alternatively bromine or iodine. The thiourea derivative IX, in which the aminocarboxylic acid grouping is preferably protected, can be used as such or in the form of a salt, especially in the form of a thiolate of an alkali metal, such as lithium, sodium or potassium, or in the form of a thiolate of an ammonium compound, in equivalent amount or in excess. A compound of the formula VIII that contains acid groups, for example when the 4-carboxyl group is unprotected or when A represents sulphomethylene, can likewise be used in the form of a salt, for example an alkali metal or ammonium salt, for example a lithium, sodium or potassium salt, or a tri-lower alkylammonium salt, such as a trimethylammonium or triethylammonium salt.

The reaction is generally carried out in a solvent, such as water, or an inert organic solvent or a mixture thereof. Suitable organic solvents are alcohols, such as methanol; ethanol or isopropanol; ketones such as acetone; ethers, such as dioxan or tetrahydrofuran, nitriles such as acetonitrile; halogenated hydrocarbons, such as methylene chloride, chloroform or carbon tetrachloride; esters, such as ethyl acetate; or amides, such as dimethylformamide or dimethylacetamide; and the like. The reaction can, if the free compounds are used, be carried out in the presence of a base. Suuitable bases are alkali metal hydroxides, such as sodium or potassium hydroxide; alkali metal carbonates, such as sodium or potassium carbonate; or organic tertiary nitrogen bases, such as tri-lower alkylamines, for example trimethylamine, triethylamine, ethyldiisopropylamine, pyridine and the like.

The reaction temperature is approximately room temperature or a lower or higher temperature, preferably between $-10°$ and $100°$ C., especially between $0°$ and $40°$ C.

The reaction can also be carried out in stages, first of all producing the open-ring intermediate of the partial formula

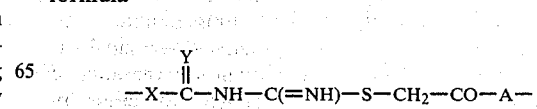

then dehydrating it in the second stage.

Process (e) (Replacement of $R_1^a$ by hydrogen)

The group $R_1^a$ in a starting material of the formula X may be free hydroxy, but is preferably esterified hydroxy. An esterified hydroxy group $R_1^a$ can be esterified by an inorganic or organic acid, such as a strong mineral acid, for example a hydrohalic acid, such as hydrochloric, hydrobromic or hydriodic acid, or an organic carboxylic or sulphonic acid, inclusive of formic acid, such as a corresponding aliphatic, cycloaliphatic, cycloaliphaticaliphatic, aromatic, araliphatic, heterocyclic or heterocyclic-aliphatic acid, or alternatively by a carbonic acid semi-derivative. $R_1^a$ thus represents, for example, halogen, such as chlorine, bromine or iodine; lower alkylsulphonyloxy, for example methylsulphonyloxy or ethylsulphonyloxy; arylsulphonyloxy, for example 4-methylphenylsulphonyloxy; lower alkanoyloxy, for example acetoxy or propionoxy; arylcarbonyloxy, for example benzoyloxy; or lower alkoxycarbonyloxy, for example methoxycarbonyloxy or ethoxycarbonyloxy.

A secondary amino group $R_1^a$ is a $-N(R_4^a)(R_4^b)$ group, in which one of the substituents $R_4^a$ and $R_4^b$ represents hydrogen and the other represents an aliphatic or cycloaliphatic hydrocarbon radical that contains up to 18, especially up to 12, and preferably up to 7, carbon atoms. Aliphatic hydrocarbon radicals $R_4^a$ or $R_4^b$ are, for example, alkyl groups, especially lower alkyl groups, optionally substituted, for example, by lower alkoxy, such as methoxy, lower alkylthio, such as methylthio, cycloalkyl, such as cyclohexyl, aryl, such as phenyl, or heterocyclyl, such as thienyl, for example methyl, ethyl, propyl, isopropyl, butyl, isobutyl, pentyl, hexyl, 2-ethoxyethyl, 2-methylthioethyl, cyclohexylmethyl, benzyl or thienylmethyl. Cycloaliphatic hydrocarbons radicals $R_4^a$ or $R_4^b$ are, for example, cycloalkyl groups optionally substituted, for example, by lower alkyl, such as methyl, lower alkoxy, such as methoxy, lower alkylthio, such as methylthio, cycloalkyl, such as cyclohexyl, aryl, such as phenyl, or heterocyclyl, such as furyl, for example cyclopropyl, cyclopentyl, cyclohexyl or cycloheptyl optionally substituted as stated.

A tertiary amino group $R_1^a$ is a $-N(R_4^a)(R_4^b)$ group in which each of the substituents $R_4^a$ and $R_4^b$ represents one of the mentioned aliphatic or cycloaliphatic hydrocarbon radicals, wherein $R_4^a$ and $R_4^b$ may be the same or different, and wherein the two substituents $R_4^a$ and $R_4^b$ may be linked to one another by a carbon-carbon bond or by an oxygen atom, a sulphur atom, or an optionally substituted, such as lower alkylated, for example methylated, nitrogen atom.

Suitable tertiary amino groups $N(R_4^a)(R_4^b)$ are, for example, dimethylamino, diethylamino, N-methylethylamino, diisopropylamino, N-methylisopropylamino, dibutylamino, N-methylisobutylamino, dicyclopropylamino, N-methylcyclopropylamino, dicyclopentylamino, N-methylcyclopentylamino, dicyclohexylamino, N-methylcyclohexylamino, N-methylcyclopentylamino, N-methylcyclohexylmethylamino, dibenzylamino, N-methylbenzylamino, N-cyclopropylbenzylamino, aziridin-1-Yl, pyrrolidin-1-yl, piperidino, 1H-2,3,4,5,6,7-hexahydroazepinyl, morpholino, thiomorpholino, piperazin-1-yl or 4-methylpiperazin-1-yl.

The substitution of the group $R_1^a$ in a compound of the formula X by hydrogen is carried out either by reducing the $C_3$–$C_4$ double bond and splitting off $R_1^a$—H, or by removing $R_1^a$ directly by hydrogenation.

The reduction of starting materials of the formula X can be carried out by using suitable reducing agents. For example, catalytically activated hydrogen can be used, the hydrogen being used in the presence of a hydrogenating catalyst, such as a palladium, nickel, rhodium, ruthenium or platinum catalyst, and, for example, hydrogen can be used together with platinum or platinum oxide in the presence of a solvent, such as an alcohol, such as a lower alkanol, for example methanol or ethanol, or acetic acid and optionally under pressure.

Preferably reduction is carried out by means of metallic reducing agents ("nascent hydrogen"), but especially with hydride reducing agents. Metallic reducing agents are, for example, reducing metals, such as sodium, potassium, calcium, magnesium, aluminium or, especially, zinc, or reducing metal compounds, for example alloys, amalgams or salts thereof, such as aluminium amalgam, which are usually used in the presence of hydrogen-yielding agents, such as water, alcohol (for example methanol or ethanol) or an acid, for example acetic acid. Zinc is used, for example, in the presence of glacial acetic acid, and an amalgam, for example, in the presence of an aqueous inert organic solvent, such as an ether. Hydride reducing agents are especially complex metal hydrides, preferably corresponding boron hydrides, such as diborane or alkali metal borohydrides, for example sodium borohydride or lithium borohydride, also zinc borohydride, and organic alkali metal aluminium hydrides, such as tri-lower alkoxy alkali metal aluminium hydrides, for example tri-tert.-butoxylithium aluminium hydride, which are usually used in the presence of solvents, especially relatively polar solvents, such as alcohols, for example lower alkanols, such as methanol or ethanol, or ethers, such as aliphatic ethers, for example glycol and polyglycol ethers, such as ethylene glycol dimethyl ether or diethylene glycol dimethyl ether, or cyclic ethers, such as tetrahydrofuran or dioxan, or solvent mixtures, also of aqueous solvents, wherein temperatures of approximately $-20°$ C. to approximately $80°$ C are used, if necessary, in a closed vessel and/or in an inert gas atmosphere, for example a nitrogen atmosphere.

If the reduction is carried out in the presence of suitable water-, acid- or amine-splitting agents, the desired 3-unsubstituted-3-cephem compound can be obtained. It is, however, also possible first of all to produce a 3-$R_1^a$ cepham compound, which can then either be isolated or further processed in situ.

Splitting off the elements of a compound of the formula $R_1^a$—H, that is to say water, an acid or an amine, from a resulting 3-$R_1^a$-cepham compound, is preferably carried out by treating with suitable water-, acid- or amine-splitting agents. Water and amines are preferably split off in the presence of an acidic agent, for example an acid, preferably a strong organic carboxylic or sulphonic acid, such as a halo-lower alkanecarboxylic acid, for example p-toluenesulphonic acid. Water is also split off in the presence of a suitable acid derivative, such as an anhydride or especially a halide, such as chloride, especially of an inorganic, for example phosphorus-containing or sulphur-containing acid, for example phosphorus oxychloride or thionyl chloride, wherein such a derivative is usually used in the presence of a base, such as a tertiary organic base, for example pyridine, or in the presence of a suitable acidic ion exchanger, such as an ion exchanger based on sulphonic acid, for example a sulphonated polystyrene ion exchanger. To split off water, it is also possible to use dehydrating carbodiimide compounds, for example, dicyclohexylcarbodiimide, or dehydrating carbonyl compounds di-substituted by way of nitrogen atoms, for example carbodiimidazole. These agents are usually used in the presence of a solvent, such as an optionally halogenated aliphatic, cycloaliphatic or aromatic hydrocarbon, for example benzene or toluene, or of a solvent mixture, it being possible to use simultaneously also as solvents suitable acidic agents, such as trifluoroacetic acid. If necessary, in addition a water-adsorbing agent or a water separator is used and the process is carried out while cooling or heating and/or in an inert gas atmosphere, for example a nitrogen atmosphere.

Preferably $R_1{}^a$ in a starting material of the formula X is an esterified hydroxy group, and after reduction or simultaneously therewith an acid of the formula $R_1{}^a$—H is split off. For this purpose, usually basic acid-splitting and/or neutralising agents are used, such as, for example, inorganic bases, such as dilute alkali metal hydroxides, for example sodium or potassium hydroxide, wherein apart from water it is also possible to use organic solvents, such as suitable ketones, for example acetone, or ethers, for example dioxan, or aqueous mixtures thereof, and to carry out the process at a pH value of a maximum of approximately 9, if necessary while cooling or heating and/or in an inert gas atmosphere, for example a nitrogen atmosphere. Preferably the acid-splitting agents used are tertiary amines, especially good proton acceptors that do not attack the lactam ring, especially tertiary aliphatic or tertiary cycloaliphatic mono- and diamines, such as tri-lower alkyl amines, for example trimethylamine, triethylamine or ethyldiisopropylamine, or bicyclic diaza compounds having an amidine-type arrangement of the ring nitrogen atoms, for example 1,5-diazabicyclo[4,3,0]non-4-ene or 1,5-diazabicyclo[5,4,0]undec-5-ene. It is also possible to use basic ion exchangers, for example based on ammonium hydroxide, as acid-splitting agents. Certain esterified hydroxy groups $R_1{}^a$, especially sulphonyloxy, for example methylsulphonyloxy groups, may be split off in the form of an acid of the formula $R_1{}^a$—H also by means of adsorption, for example on silica gel, aluminium oxide etc., and elution (chromatography).

The reactions for splitting off acid are carried out in the absence, but usually in the presence, of a solvent, such as an optionally halogenated hydrocarbon of aliphatic, cycloaliphatic or aromatic character, such as methylene chloride, a lower alkanone, for example acetone, or an ether, for example tetrahydrofuran or dioxan, or of a solvent mixture, including an aqueous mixture, if necessary while cooling or heating and/or in an inert gas atmosphere, for example a nitrogen atmosphere.

Preferably in a compound of the formula X an esterified hydroxy group $R_1{}^a$, such as a 3-halosulphonyloxy, for example a 3-chlorosulphonyloxy or 3-bromosulphonyloxy, a 3-toluenesulphonyloxy or a 3-methanesulphonyloxy group, can be replaced by hydrogen by treating with zinc in glacial acetic acid, and a tertiary amino group $R_1{}^a$, such as 3-morpholino, 3-pyrrolidino or 3-N-methylcyclohexylamino, by treating with diborane and then glacial acetic acid.

Process (f) (Cyclisation according to Wittig):

In the starting material of the formula XI each of the groups $R_a$, $R_b$ and $R_c$ represents especially a lower alkyl radical optionally substituted by functional groups, for example by optionally etherified or esterified hydroxy groups, such as lower alkoxy groups and/or halogen atoms, or a phenyl radical optionally substituted, for example, by aliphatic hydrocarbon radicals, such as lower alkyl groups, and/or by functional groups, such as optionally etherified or esterified hydroxy groups, such as lower alkoxy groups or halogen atoms, or by nitro groups. $R_a$, $R_b$ and $R_c$ are preferably phenyl groups.

The cyclisation is carried out in an inert organic solvent, at temperatures between approximately $-20°$ C. and approximately 100° C., usually directly after the oxidative formation of the terminal oxo group from a corresponding terminal hydroxy group.

Process (g) (Cyclisation with the splitting off of $Y^o$ and $Z^o$)

In a starting compound of the formula XII, $Z^o$ is hydrogen or halogen, such as chlorine, bromine or iodine, and $Y^o$ is, for example, a —S—$R_4$ group, a —SO$_2$—$R_5$ group bonded by the sulphur atom to the thio group —S—, or a —S—SO$_2$—$R_5$ group.

In the —S—$R_4$ group $R_4$ is an optionally substituted aromatic heterocyclic radical having up to 15, preferably up to 9, carbon atoms, and at least one ring nitrogen atom and optionally a further ring hetero atom, such as oxygen or sulphur, which radical is bonded by one of its ring carbon atoms, which is bonded by a double bond to a ring nitrogen atom, to the thio group —S—, or is an acyl radical of an organic carboxylic or thiocarboxylic acid, such as an optionally substituted, aliphatic, cycloaliphatic, araliphatic or aromatic, carboxylic or thiocarboxylic acid having up to 18, preferably up to 10, carbon atoms.

Radicals $R_4$ of this type are, for example, monocyclic five-membered thiatriazacyclic, oxadiazacyclic or oxatriazacyclic radicals of aromatic character, but especially monocyclic five-membered diazacyclic, oxazacyclic and thiazacyclic radicals of aromatic character, and/or especially the corresponding benzdiazacyclic, benzoxazacyclic or benzthiazacyclic radicals, in which the heterocyclic moiety is five-membered and of aromatic character, wherein in radicals $R_4$ a substitutable ring nitrogen atom may be substituted, for example, by lower alkyl. Examples of such groups $R_4$ are 1-methylimidazol-2-yl, 1,3-thiazol-2-yl, 1,3,4-thiadiazol-2-yl, 1,3,4,5-thiatriazol-2-yl, 1,3-oxazol-2-yl, 1,3,4-oxadiazol-2-yl, 1,3,4,5-oxatriazol-2-yl, quinol-2-yl, 1-methylbenzimidazol-2-yl, benzoxazol-2-yl and especially benzthiazol-2-yl.

Examples of acyl or thioacyl radicals $R_4$ are lower alkanoyl, including formyl, acetyl and propionyl; lower thioalkanoyl, for example thioacetyl or thiopropionyl; cycloalkanecarbonyl, for example cyclohexanecarbonyl; cycloalkanethiocarbonyl, for example cyclohexanethiocarbonyl; benzoyl; thiobenzoyl; naphthylcarbonyl; naphthylthiocarbonyl; heterocyclic carbonyl or thiocarbonyl, such as pyrid-2-ylcarbonyl, pyrid-3-ylcarbonyl or pyrid-4-ylcarbonyl, 2- or 3-thenoyl, 2- or 3-furoyl, pyrid-2-ylthiocarbonyl, pyrid-3-ylthiocarbonyl, pyrid-4-ylthiocarbonyl, 2- or 3-thiothenoyl, 2- or 3-thiofuroyl; or corresponding acyl or thioacyl group monosubstituted or poly-substituted, for example by lower alkyl, such as methyl, by halogen, such as fluorine or chlorine, by lower alkoxy, such as methoxy, by aryl, such as phenyl or by aryloxy, such as phenoxy.

In the groups —SO$_2$—$R_5$ and —S—SO$_2$—$R_5$, $R_5$ is an optionally substituted, especially aliphatic, cycloaliphatic, araliphatic or aromatic, hydrocarbon radical having up to 18, preferably up to 10, carbon atoms. Suitable $R_5$ groups are, for example, alkyl groups, especially lower alkyl, such as methyl, ethyl or butyl groups, alkenyl groups, such as allyl or butenyl groups and cycloalkyl groups, such as cyclopentyl or cyclohexyl groups, optionally mono-substituted or poly-substituted, for example, by lower alkoxy, such as methoxy, by halogen, such as fluorine, chlorine or bromine, by aryl, such as phenyl, or by aryloxy, such as phenoxy; or naphthyl or especially phenyl groups optionally mono-substituted or poly-substituted by lower alkyl, such as methyl, by lower alkoxy, such as methoxy, by halogen, such as fluorine, chlorine or bromine, by aryl, such as phenyl, by aryloxy, such as phenoxy or by nitro, for example phenyl, o-, m- or preferably p-tolyl, o- m- or preferably p-methoxyphenyl, o-, m- or p-chlorophenyl, p-biphenylyl, p-phenoxyphenyl, p-nitrophenyl or 1- or 2-naphthyl.

In a compound of the formula XII, the group $R_1$ may be in the trans-position (crotonic acid configuration) or in the cis-position (isocrotonic acid configuration) to the carboxyl group. The cyclisation with the splitting off of $Y^o$ and $Z^o$ is effected by means of a suitable base, especially a strong organic base or inorganic base. Attention is drawn in particular to bicyclic amidines, such as diazabicycloalkenes, for example 1,5-diazabicyclo[4,3,0]non-5-ene or 1,5-diazabicyclo[5,4,0]undec-5-ene; guanidines substituted, for example, by one or more lower alkyl groups, such as tetramethylguanidine; metal bases, such as hydrides, amides or alcoholates of alkali metals, especially of lithium, sodium or potassium, for example sodium hydride, lithium di-lower alkylamides, such as lithium diisopropylamide, potassium lower alkanolates, such as potassium tert.-butylate; and tertiary organic nitrogen bases, for example tri-lower alkylamines, such as triethylamine.

The reaction is carried out in a suitable inert solvent, for example in an aliphatic, cycloaliphatic or aromatic hydrocarbon, such as hexane, cyclohexane, benzene or toluene; a halogenated hydrocarbon, such as methylene chloride; an ether, such as di-lower alkyl ether, for example diethyl ether; a di-lower alkoxy-lower alkane, such as dimethoxyethane; a cyclic ether, such as dioxan or tertahydrofuran; or a lower alkanol, for example methanol, ethanol or tert.-butanol; or in a mixture thereof; at room temperature or while heating slightly to 40° to 50°, if desired in an inert gas atmosphere, such as a nitrogen atmosphere.

Process (h) (Isomerisation)

In a 2-cephem compound of the formula XIII, the optionally protected carboxyl group in the 4-position preferably has the α-configuration.

2-cephem compounds of the formula XIII are isomerised by treating them with a slightly basic agent, and isolating the corresponding 3-cephem compound. Suitable isomerising agents are, for example, organic nitrogen-containing bases, especially tertiary heterocyclic bases of aromatic character, more especially bases of the pyridine type, such as pyridine itself, and collidines or lutidines, and also quinoline; tertiary aromatic bases, for example those of the aniline type, such as N,N-di-lower alkylanilines, for example N,N-dimethylaniline or N,N-diethylaniline; or tertiary aliphatic, azacycloaliphatic or aralphatic bases, such as N,N,N-trilower alkylamines, for example N,N,N-trimethylamine, N,N-diisopropyl-N-ethylamine; N-lower alkylazacycloalkanes, for example N-methylpiperidine; or N-phenyl-lower alkyl-N,N-di-lower alkylamines, for example N-benzyl-N,N-dimethylamine; and mixtures thereof, such as the mixture of a base of the pyridine type and a N,N,N-tri-lower alkylamine, for example pyridine and triethylamine. It is also possible to use inorganic or organic salts of bases, especially of medium strength to strong bases with weak acids, such as alkali metal or ammonium salts of lower alkanecarboxylic acids, for example sodium acetate, triethylammonium acetate or N-methylpiperidine acetate, and other analogous bases or mixtures of such basic agents.

When isomerising with basic agents, the process is preferably carried out in an anhydrous medium, in the presence or absence of a solvent, such as an optionally halogenated, for example chlorinated, aliphatic, cycloaliphatic or aromatic hydrocarbon, or of a solvent mixture, wherein the bases, liquid under the reaction conditions, used as reactants may simultaneously also serve as solvents; the process is carried out while cooling, at room temperature or while heating, preferably in a temperature range of approximately −30° C. to approximately 100° C., in an inert gas atmosphere, for example a nitrogen atmosphere, and/or in a closed vessel.

The 3-cephem compounds obtainable in this manner may be separated from 2-cephem compounds optionally still present in a manner known per se, for example by adsorption and/or crystallisation.

The isomerisation of 2-cephem compounds of the formula XIII is preferably carried out by oxidising these in the 1-position, if desired separating a resulting isomeric mixture of the 1-oxides, and reducing the resulting 1-oxides of the corresponding 3-cephem compounds.

Suitable oxidising agents for oxidising 2-cephem compounds in the 1-position are inorganic peracids that have a reduction potential of at least 1.5 volts and consist of non-metallic elements, organic peracids, or mixtures of hydrogen peroxide and acids, especially organic carboxylic acids, with a dissociation constant of at least $10^{-5}$. Suitable inorganic peracids are periodic acid and persulphuric acid. Organic peracids are corresponding percarboxylic and persulphonic acids that are added as such or can be formed in situ by using at least one equivalent of hydrogen peroxide and a carboxylic acid. It is advantageous to use a large excess of the carboxylic acid if, for example, acetic acid is used as solvent. Suitable peracids are, for example, performic acid, peracetic acid, trifluoroperacetic acid, permaleic acid, perbenzoic acid, 3-chloroperbenzoic acid, monoperphthalic acid or p-toluenepersulphonic acid.

Oxidation can also be carried out using hydrogen peroxide with catalytic amounts of an acid having a dissociation constant of at least $10^{-5}$, and it is possible to use low concentrations, for example 1-2% or less, or larger amounts of the acid. The activity of the mixture depends especially on the strength of the acid. Suitable mixtures are, for example, those of hydrogen peroxide with acetic acid, perchloric acid or trifluoroacetic acid.

The above oxidation can be carried out in the presence of suitable catalysts. For example, the oxidation with percarboxylic acids can be catalysed by the presence of an acid having a dissociation constant of at least $10^{-5}$, its activity depending on its strength. Acids suitable as catalysts are, for example, acetic acid, perchloric acid and trifluoroacetic acid. Usually at least equimolar amounts of the oxidising agent are used, and preferably a small excess of approximately 10% to approximately 20%, but it is also possible to use larger excesses, that is up to ten times the amount of oxidising agent or more. The oxidation is carried out under mild conditions, for example at temperatures of approximately −50° C. to approximately 100° C., preferably from approximately −10° to approximately 40° C.

The reduction of the 1-oxides of 3-cephem compounds can be carried out in a manner known per se by treating with a reducing agent, if necessary in the presence of an activating agent. Suitable reducing agents are, for example: catalytically activated hydrogen, wherein noble metal catalysts that contain palladium, platinum or rhodium are used, and these are optionally used together with a suitable carrier, such as carbon or barium sulphate; reducing tin, iron, copper or manganese cations, which are used in the form of corresponding compounds or complexes of inorganic or organic nature, for example in the form of tin(II) chloride, fluoride, acetate or formate, iron(II) chloride, sulphate, oxalate or succinate, copper(I) chloride, benzoate or oxide, or manganese(II) chloride, sulphate, acetate or oxide; or in the form of complexes, for example with ethylenediaminetetraacetic acid or nitrolotriacetic acid; reducing dithionite, iodine or iron(II) cyanide anions, which are used in the form of corresponding inorganic or organic salts, such as alkali metal salts, for example sodium or potassium dithionite, sodium or potassium iodide or sodium or potassium ferrocyanide, or in the form of the corresponding acids, such as hydriodic acid; reducing trivalent inorganic or organic phosphorus compounds, such as phosphines, esters, amides and halides of phosphinous, phosphonous or phosphorous acid, as well as phosphorus/sulphur compounds corresponding to these phosphorus oxygen compounds, in which organic radicals are especially aliphatic, aromatic or araliphatic radicals, for example optionally substituted lower alkyl, phenyl or phenyl-lower alkyl groups, such as, for example, triphenylphosphine, tri-n-butylphosphine, diphenylphosphinous acid methyl ester, diphenylchlorophosphine, phenyldichlorophosphine, benzenephosphonous acid dimethyl ester, butanephosphonous acid methyl ester, phosphorous acid triphenyl ester, phosphorous acid trimethyl ester, phosphorus trichloride, phosphorus tribromide etc.; reducing halosilane compounds that have at least one silicon-bonded hydrogen atom, and that apart from the halogen atom, such as chlorine, bromine or iodine, may also contain organic radicals, such as aliphatic or aromatic groups, for example optionally substituted or aromatic groups, for example optionally substituted lower alkyl groups or phenyl groups, such as chlorosilane, bromosilane, dichlorosilane or trichlorosilane, dibromosilane or tribromosilane, diphenylchlorosilane, dimethylchlorosilane, trimethyliodosilane or also halosilane compounds in which all the hydrogen atoms are replaced by organic radicals, such as tri-lower alkyl-halosilane, for example trimethyliodosilane, or cyclic, sulphur-containing silanes, such as 1,3-dithia-2,4-disilacyclobutanes or 1,3,5-trithia-2,4,6-trisilacyclohexanes, of which the silicon atoms are substituted by hydrocarbon radicals, such as especially lower alkyl radicals, for example 2,2,4,4-tetramethyl-1,3-dithia-2,4-disilacyclobutane or 2,2,4,4,6,6-hexamethyl-1,3,5-trithia-2,4,6-trisilacyclohexane, etc.; reducing quaternary chloromethyleneiminium salts, especially chlorides or bromides, in which the iminium group is substituted by a divalent or two monovalent organic radicals, such as optionally substituted lower alkylene or lower alkyl groups, such as N-chloromethylene-N,N-diethyliminium chloride or N-chloromethylenepyrrolidinium chloride; and complex metal hydrides, such as sodium borohydride, in the presence of suitable activating agents, such as cobalt(II) chloride, and borane dichloride.

As activating agents that are used together with those of the above reducing agents that do not themselves have Lewis acid properties, that is to say that are used especially with the dithionite, iodine or iron(II) cyanide reducing agents and the non-halogen-containing trivalent phosphorus reducing agents and in the case of catalytic reduction, special mention is given to organic carboxylic and sulphonic acid halides, sulphur, phosphorus or silicon halides with the same second order hydrolysis constant as benzoyl chloride or a larger second order hydrolysis constant than benzoyl chloride, for example phosgene, oxalyl chloride, acetic acid chloride or bromide, chloroacetic acid chloride, pivalic acid chloride, 4-methoxybenzoic acid chloride, 4-cyanobenzoic acid chloride, p-toluenesulphonic acid chloride, methanesulphonic acid chloride, thionyl chloride, phosphorus oxychloride, phosphorus trichloride, phosphorus tribromide, phenyldichlorophosphine, benzenephosphonous acid dichloride, dimethylchlorosilane or trichlorosilane, and also suitable acid anhydrides, such as trifluoroacetic acid anhydride, or cyclic sultones, such as ethanesultone, 1,3-propanesultone, 1,4-butanesultone or 1,3-hexanesultone.

The reduction is preferably carried out in the presence of solvents or mixtures thereof, the choice of which is governed especially by the solubility of the starting materials and by the choice of reducing agent, for example in lower alkanecarboxylic acids or esters thereof, such as acetic acid or ethyl acetate, in the case of catalytic reduction, and, for example, in optionally substituted, such as halogenated or nitrated, aliphatic, cycloaliphatic, aromatic or araliphatic hydrocarbons, for example benzene, methylene chloride, chloroform or nitromethane; suitable acid derivatives, such as lower alkanecarboxylic acid esters or nitriles, for example ethyl acetate or acetonitrile; or amides of inorganic or organic acids, for example dimethylformamide or hexamethylphosphoric amide; ethers, for example diethyl ether, tetrahydrofuran or dioxan; ketones, for example acetone; or sulphones, especially aliphatic sulphones, for example dimethylsulphone or tetramethylenesulphone, etc. together with the chemical reducing agents, wherein these solvents preferably do not contain water. The reduction is usually carried out at temperatures from approximately −20° C. to approximately 100° C., wherein if very reactive activating agents are used the reaction can be carried out at lower temperatures.

Subsequent operations

In a resulting intermediate of the formula I in which at least one of the functional groups is present in protected form, still unprotected functional groups may be protected in a customary manner that is known per se, or protecting groups that are present may be exchanged for others, for example by splitting off the protecting group present and introducing the desired other protecting group.

1. Esterification of the 4-carboxyl group

The conversion of a free carboxyl group in a resulting compound of the formula I into an esterified carboxyl group that can be split under physiological conditions is carried out in accordance with esterification methods that are known per se, for example, by esterifying a compound of the formula I in which other functional groups, such as amino, hydroxy or sulpho groups, are optionally present in protected form, or a functional derivative thereof that is reactive with respect to the carboxyl group to be esterified, or a salt thereof, with a corresponding alcohol or a reactive functional derivative thereof.

2. Oxidation of the hydroxymethylene group A

In a resulting compound of the formula I in which functional groups are protected, oxidation of the hydroxymethylene group A can be carried out in a manner known for the oxidation of hydroxy groups to form oxo groups. Suitable oxidising agents are oxidising oxides, such as those of manganese, chromium, nitrogen or sulphur, such as manganese dioxide, chromium trioxide, for example Jones reagent or chromium trioxide in the presence of acetic acid, sulphuric acid or pyridine, dinitrogen tetroxide, dimethyl sulphoxide optionally in the presence of dicyclohexylcarbodiimide or oxygen, and peroxides, such as hydrogen peroxide; and oxygen-containing acids, such as permanganic acid, chromic acid or hypochloric acid, or salts thereof, such as potassium permanganate, sodium or potassium dichromate or potassium hypochlorite. The hydroxymethylene group may be converted into the oxomethylene group also by Oppenauer oxidation, that is to say by treating with the salt of a sterically hindered alcohol, such as aluminium or potassium tertiary butoxide, isopropoxide or phenoxide in the presence of a ketone, such as acetone, cyclohexanone or fluorenone. Another possibility of converting the hydroxymethylene group into the oxomethylene group consists in dehydrogenating, for example with Raney nickel.

Depending on the oxidising agent, the oxidation is carried out in water or an optionally aqueous solvent at temperatures of approximately 0° to approximately 100°.

3. Conversion of the oxomethylene group A by hydroxylamines

In a resulting compound of the formula I in which functional groups are protected and in which A represents an oxomethylene group, this can be converted into a hydroxyiminomethylene group or a $R^o$-substituted hydroxyiminomethylene group by treating with hydroxylamine or a substituted hydroxylamine of the formula $R^o$—O—$NH_2$, respectively.

The reaction of the oxomethylene group with the hydroxylamine compound is carried out in the usual manner, for example by allowing the two reactants to react in a solvent, such as water, or an organic solvent, such as an alcohol, for example methanol, at slightly elevated or reduced temperature, optionally in an inert gas atmosphere, such as a nitrogen atmosphere. The hydroxylamine compound may be liberated, also in situ, from one of its salts, for example a hydrohalide, such as hyddrochloride, by treating with an inorganic base, such as an alkali metal hydroxide, for example sodium hydroxide, or with an organic base, such as a tertiary amine, for example a tri-lower alkylamine, such as triethylamine or ethyldiisopropylamine, or with a heterocyclic tertiary base, such as pyridine.

4. Nitrosation and sulphonation of the methylene group A:

In a resulting compound of the formula I in which functional groups are protected and in which A represent methylene, the methylene group can be converted into a hydroxyiminomethylene group by nitrozation, for example by treating with a nitrite, such as amyl nitrite, in the presence of a base, for example in a manner analogous to that described in BE-PS No. 855 953, and the hydroxyiminomethylene group can then, if desired, be converted by alkylation into a $R^o$—O—N=C= group, for example into a methoxyiminomethylene group by alkylating with dimethyl sulphate in the presence of a base. Also, a methylene group A may be sulphonated to form a sulphomethylene group, for example, by treating with the $SO_3$/dioxan complex, for example in a manner analogous to that described in DT-OS No. 2 638 028.

5. Esterification of the 3-hydroxy group

In a resulting compound of the formula I in which functional groups are protected and in which $R_1$ represents a protected hydroxy group, this hydroxy-protecting group may be split off and replaced by hydrogen. The resulting free hydroxy group may be converted according to conventional methods into an esterified or etherified hydroxy group $R_1$.

The esterification of the free hydroxy group $R_1$ is carried out with an acylating agent that introduces the desired acyl radical. In this process the corresponding organic carboxylic acid or a reactive acid derivative thereof is used, such as a halide, for example a fluoride or chloride, or a pseudo-halide, such as a cyanocarbonyl compound corresponding to the carboxylic acid, or an anhydride (which is also to include an inner anhydride of a carboxylic acid, that is a ketone, or of carbamic or thiocarbamic acid, that is an isocyanate, or a mixed anhydride, such as one that may be formed, for example, with a haloformic acid lower alkyl ester, such as a chloroformic acid ethyl ester or isobutyl ester, or with trichloroacetic acid chloride) or an activated ester, wherein, if necessary, the process is carried out in the presence of suitable condensing agents, when using acids, for example in the presence of carbodiimide compounds, such as dicyclohexylcarbodiimide, or carbonyl compounds, such as diimidazolylcarbonyl, and when using reactive acid derivatives, for example in the presence of basic agents, such as tri-lower alkylamines, for example triethylamine, or heterocyclic bases, for example pyridine. The acylation can be carried out in the absence or presence of a solvent or solvent mixture, while cooling, at room temperature or while heating and, if necessary, in a closed vessel and/or in an inert gas atmosphere, for example a nitrogen atmosphere. Suitable solvents are, for example, optionally substituted, especially optionally chlorinated, aliphatic, cycloaliphatic or aromatic hydrocarbons, such as benzene or toluene, it being possible to use suitable esterifying reagents, such as acetic acid anhydride, also as diluents.

By means of organic sulphonic acids, for example lower alkanesulphonic acids, such as methanesulphonic acid, or aromatic sulphonic acids, such as p-toluenesulphonic acid, esterified hydroxy groups may be formed, preferably by treating with a reactive sulphonic acid derivative, such as a corresponding halide, for example a chloride, if necessary in the presence of an acid-neutralising basic agent, for example an inorganic or organic base, for example in an analogous manner to the esters with carboxylic acids.

6. Etherification of the 3-hydroxy group

The etherification of the free hydroxy group $R_1$ is carried out with a conventional etherifying agent introducing the desired hydrocarbon.

Suitable etherifying agents are, for example, corresponding diazo compounds, such as optionally substituted diazo-lower alkanes, for example diazomethane, diazoethane, diazo-n-butane or diphenyldiazomethane. These reagents are used in the presence of a suitable inert solvent, such as an aliphatic, cycloaliphatic or aromatic hydrocarbon, such as hexene, cyclohexane, benzene or toluene, a halogenated aliphatic hydrocarbon, for example methylene chloride, or an ether, such as a di-lower alkyl ether, for example diethyl ether, or a cyclic ether, for example tetrahydrofuran or dioxan, or a solvent mixture, and, depending on the diazo reagent, while cooling, at room temperature or while heating slightly and also, if necessary, in a closed vessel and/or in an inert gas atmosphere, for example a nitrogen atmosphere.

Other suitable etherifying agents are esters of corresponding alcohols, especially those with strong inorganic or organic acids, such as mineral acids, for example hydrohalic acids, such as hydrochloric, hydrobromic or hydriodic acid, also sulphuric acid or halosulphuric acids, for example fluorosulphuric acid, or strong organic sulphonic acids, such as lower alkanesulphonic acids optionally substituted, for example, by halogen, such as fluorine, or aromatic sulphonic acids, such as, for example, benzenesulphonic acids optionally substituted, for example, by lower alkyl, such as methyl, by halogen, such as bromine, and/or by nitro, for example methanesulphonic acid, trifluoromethanesulphonic acid or p-toluenesulphonic acid, for example, di-lower alkyl sulphates, such as dimethyl sulphate, also fluorosulphonic acid lower alkyl esters, for example fluorosulphonic acid methyl ester or optionally halogen-substituted methanesulphonic acid lower alkyl esters, for example trifluoromethanesulphonic acid methyl ester. They are normally used in the presence of an inert solvent, such as an optionally halogenated, such as chlorinated, aliphatic, cycloaliphatic or aromatic hydrocarbon, for example methylene chloride, an ether, such as dioxan or tetrahydrofuran, or a mixture thereof. In this process suitable condensing agents are preferably used, such as alkali metal carbonates or bicarbonates, for example sodium or potassium carbonate or bicarbonate (usually together with a sulphate), or organic bases, such as, normally sterically hindered, tri-lower alkylamines, for example N,N-diisopropyl-N-ethylamine (preferably together with lower alkyl halosulphates or optionally halogen-substituted methanesulphonic acid lower alkyl esters), the process being carried out while cooling, at room temperature, or while heating, for example at temperatures of approximately $-20°$ C. to approximately $50°$ C. and, if necessary, in a closed vessel and/or in an inert gas atmosphere, for example a nitrogen atmosphere.

Other etherifying agents are corresponding acetals, for example gem-lower alkoxy-lower alkanes, such as 2,2-dimethoxypropane, which are used in the presence of a strong organic sulphonic acid, such as p-toluenesulphonic acid, and a suitable solvent, such as a di-lower alkyl sulphoxide or lower alkylene sulphoxide, for example dimethyl sulphoxide; or ortho esters, for example orthoformic acid tri-lower alkyl esters, for example orthoformic acid triethyl ester, which are used in the presence of a strong mineral acid, for example sulphuric acid, or a strong organic sulphonic acid, such as p-toluenesulphonic acid, and a suitable solvent, such as an ether, for example dioxan.

Other etherifying agents are corresponding tri-$R_1^o$-oxonium salts (so-called Meerwein salts), di-$R_1^o$—O—carbenium salts or di-$R_1^o$-halonium salts, in which $R_1^o$ represents the radical to be introduced, for example trilower alkyloxonium salts, and di-lower alkoxycarbenium or di-lower alkylhalonium salts, especially the corresponding salts with complex fluorine-containing acids, such as the corresponding tetrafluoroborates, hexafluorophosphates, hexafluoroantimonates or hexachloroantimonates. Reagents of this type are, for example, trimethyloxonium or triethyloxonium hexafluoroantimonate, hexachloroantimonate, hexafluorophosphate or tetrafluoroborate, dimethoxycarbenium hexafluorophosphate or dimethylbromonium hexafluoroantimonate. These etherifying agents are preferably used in an inert solvent, such as an ether or a halogenated hydrocarbon, for example diethyl ether, tetrahydrofuran or methylene chloride, or in a mixture thereof, if necessary in the presence of a base, such as an organic base, for example a preferably sterically hindered tri-lower alkylamine, for example N,N-diisopropyl-N-ethylamine, and while cooling, at room temperature or while heating slightly, for example at approximately $-20°$ C. to approximately $50°$ C., if necessary in a closed vessel and/or in an inert gas atmosphere, for example a nitrogen atmosphere.

Other etherifying agents are, finally, corresponding 1-$R_1^o$-3-aryltriazene compounds, in which $R_1^o$ represents the radical to be introduced and aryl preferably represents an optionally substituted phenyl radical, for example lower alkylphenyl, such as 4-methylphenyl. Triazene compounds of this type are 3-aryl-1-lower alkyltriazenes, for example 3-(4-methylphenyl)-1-ethyltriazene, 3-(4-methylphenyl)-1-n-propyltriazene or 3-(4-methylphenyl)-1-isopropyltriazene. These reagents are usually used in the presence of inert solvents, such as optionally halogenated hydrocarbons or ethers, for example benzene, or solvent mixtures, and while cooling, at room temperature and preferably at elevated temperature, for example at approximately $20°$ C. to approximately $100°$ C., if necessary in a closed vessel and/or in an inert gas atmosphere, for example a nitrogen atmosphere.

7. Halogenation of the 3-position

In a resulting compound of the formula I in which $R_1$ represents a free or sulphonated hydroxy group and in which other functional groups are protected, this free or sulphonated hydroxy group can be exchanged for halogen.

The substitution of the free hydroxy group $R_1$ by halogen can be carried out in a variety of ways, usually by treating with a halogenating, that is fluorinating, chlorinating or brominating, agent.

Suitable halogenating agents are, for example, phosphorus reagents replacing enol-hydroxyl groups by halogen, such as dihalotriorganophosphoranes, trihalodiorganophosphoranes or a mixture consisting of a triorganophosphine and a tetrahalomethane.

Examples of the mentioned phosphoranes are difluorotriphenylphosphorane, trifluorodiphenylphosphorane, dichlorotriphenylphosphorane, trichlorodiphenylphosphorane, dibromotriphenylphosphorane and tribromodiphenylphosphorane, in which one of the phenyl groups may be substituted by a polymer, such as a polystyrene crosslinked with divinylbenzene, or by dimethylaminomethyl.

Examples of the mentioned phosphines are triethylphosphine, methylpropylphenylphosphine, bis-(3-dimethylaminopropyl)phenylphosphine, tris-(dimethylamino)phosphine, bis-(dimethylamino)phenylphosphine and especially triphenylphosphine, wherein one of the phenyl groups may be substituted by a polymer, such as a polystyrene crosslinked with divinylbenzene.

Tetrahalomethanes are, for example, carbon tetrabromide and especially carbon tetrachloride.

The reaction with the halogenated phosphorus reagents is carried out in a manner known per se in an inert, aprotic, preferably polar, solvent, such as a chlorinated hydrocarbon, for example methylene chloride, chloroform, carbon tetrachloride, 1,2-dichloroethane, a nitrile, such as acetonitrile or benzonitrile, or an N,N-di-substituted carboxylic acid amide, such as dimethylformamide or N,N-dimethylacetamide, or mixtures thereof, depending on the reactivity of the reagent used while cooling or heating, that is to say at temperatures between approximately −60° C. up to the reflux temperature of the solvent used, optionally in an inert gas atmosphere, such as a nitrogen atmosphere. When using tri-lower alkylphosphines or tris-(di-lower alkylamine)-phosphines and carbon tetrachloride or carbon tetrabromide cooling, approximately to −60° to −20° C., is usually necessary.

When halogenating with the mentioned phosphoranes, a weak base, such as pyridine or a N,N-di-lower alkylaniline, such as N,N-dimethylaniline, may be added to the reaction medium in order to bind resulting hydrogen halide.

Other halogenating agents are corresponding N,N-disubstituted halo-iminium halide compounds, especially of the formula $[(CH_3)_2N=CH \text{ Hal}]^{\oplus} \text{Hal}^{\ominus}$, in which Hal is chlorine or bromine.

The above reagent is usually produced in situ by treating a suitable N,N-di-substituted amide, especially dimethylformamide, with a chlorinating or brominating agent, such as, for example, phosgene, carbonyl dibromide, oxalyl chloride, oxalyl bromide, thionyl chloride, thionyl bromide phosphorus trichloride, phosphorus oxychloride, phosphorus tribromide, phosphorus oxybromide or phosphorus pentachloride, especially with phosphorus trichloride or phosphorus tribromide.

The above reaction is usually carried out in the presence of a solvent or diluent, wherein apart from the amide used as solvent and normally present in excess, usually dimethylformamide or alternatively dimethylacetamide, it is possible to use also ethereal solvents, for example tetrahydrofuran or dioxon, halogenated hydrocarbons, for example methylene chloride, or sulphoxides, for example dimethyl sulphoxide.

The chlorinating agent and brominating agent are normally added in quantities corresponding to two equivalents of the 3-hydroxy-3-cephem starting material. The reaction can be carried out, for example, by adding the chlorinating agent or brominating agent while cooling to a solution of the 3-hydroxy-3-cephem starting material in dimethylformamide and then leaving the reaction mixture to stand for a few hours at room temperature.

The chlorination or bromination may also be carried out by first of all mixing the chlorinating or brominating agent with the amide, especially dimethylformamide, and thus forming the halo-iminium halide, whereupon the solution of the 3-hydroxy-3-cephem starting material in the amide, especially in dimethylformamide, to which an additional solvent may also be added, or in another solvent, for example tetrahydrofuran, is added. If necessary the reactions are carried out in an inert gas atmosphere.

The conversion of the free hydroxy group $R_1$ into fluorine can be carried out, for example, by treating with a reagent of the formula $F_3S$-Am, in which Am represents a di-substituted amino group; reagents of this type are described, inter alia, by Markovskij et al., Synthesis, volume 1973, page 787. The group Am represents especially di-lower alkylamino, for example dimethylamino, diethylamino, ethylmethylamino, methylpropylamino, di-n-propylamino or diisopropylamino; lower alkylphenylamino, for example methylphenylamino or ethylphenylamino; lower alkyleneamino, for example pyrrolidono or piperidino; oxa-lower alkyleneamino, for example morpholino; or optionally aza-lower alkyl-substituted amino, for example 4-methylpiperazino.

The reaction is preferably carried out in a suitable inert solvent, such as an optionally substituted hydrocarbon, for example cyclopentane, cyclohexane, benzene, toluene, xylene, chlorobenzene, dichlorobenzene, pentane, hexane, chloroform and especially methylene chloride or an ether, such as diethyl ether, tetrahydrofuran or, especially, dioxan, if necessary while cooling or heating for example in a temperature range of approximately −20° C. to approximately 80° C., preferably from approximately 0° C. to approximately 30° C., and/or in an inert gas atmosphere.

A sulphonated hydroxy group $R_1$ may be converted into fluorine by treating with an inorganic fluoride in the presence of a crown ether.

A sulphonated hydroxy group $R_1$ is especially lower alkylsulphonyloxy, especially methylsulphonyloxy, but may alternatively be arylsulphonyloxy, in which aryl is preferably phenyl optionally substituted, for example, by lower alkyl, such as methyl, by halogen, for example bromine, or by nitro, for example 4-methylphenylsulphonyloxy.

An inorganic fluoride is especially a metal fluoride, wherein especially an alkali metal fluoride, for example sodium fluoride, or a heavy metal fluoride, for example silver fluoride, is used.

The crown ethers used together with the inorganic fluoride are optionally substituted 18-crown-6-ethers, such as dicyclohexyl-18-crown-6-ether.

The reaction is carried out in the presence of an inert solvent, especially a nitrile, for example acetonitrile or propionitrile, or a nitro-lower alkane, for example nitromethane or nitroethane, under substantially anhydrous conditions and, if necessary, while cooling, for example in a temperature range of approximately −20° C. to approximately 25° C., preferably at approximately room temperature and optionally in an inert gas atmosphere.

8. Thiolisation of the 3-position

In a resulting compound of the formula I in which functional groups are protected, an esterified or etherified hydroxy group $R_1$ substitutable by a thiol may be converted into an etherified mercapto group $R_1$ by treating with a thiol.

An esterified hydroxy group $R_1$ substitutable by a thiol is esterified by one of the mentioned inorganic or organic acids, for example by a hydrohalic acid, an acid containing sulphur or phosphorus, such as a sulphuric or sulphonic acid, a phosphoric, phosphonic or phosphinic acid, or a carboxylic acid. An etherified hydroxy group $R_1$ substitutable by a thiol is etherified by one of the mentioned hydrocarbon radicals, for example by an aliphatic, cycloaliphatic, aromatic or araliphatic hydrocarbon radical having, for example, up to 15 carbon atoms, such as $C_1$–$C_4$-lower alkyl, for example methyl or ethyl, $C_2$–$C_6$-lower alkenyl, for example vinyl or propenyl, $C_3$–$C_7$-cycloalkyl, for example cyclopropyl or cyclohexyl, phenyl, or phenyl-lower alkyl, such as benzyl.

Preferably the radical $R_1$ substitutable by thiol is chlorine, bromine, lower alkanesulphonyloxy, such as methanesulphonyloxy or ethanesulphonyloxy, or arylsulphonyloxy, such as benzenesulphonyloxy, p-toluenesulphonyloxy, p-chlorobenzenesulphonyloxy or p-nitrobenzenesulphonyloxy.

The substitution of this group $R_1$ by the etherified mercapto group may be carried out in a manner known per se while cooling, at room temperature or while heating, that is at temperatures between 0° C. and approximately 40° C., in a suitable inert solvent and in the presence of a base. Suitable bases are especially sterically hindered amines, such as tri-lower alkylamines, for example N,N-diisopropyl-N-ethylamine, bicyclic amidines, such as diazabicycloalkanes, for example 1,5-diazabicyclo[4,3,0]non-5-ene or 1,5-diazabicyclo[5,4,0]undec-5-ene, and alkali metal hydrides, amides or lower alkanolates, such as sodium hydride, sodium or lithium amide, sodium ethylate or potassium tert.-butylate. The reaction can be carried out in an inert gas atmosphere, such as a nitrogen atmosphere, and, if necessary, in a closed vessel under pressure.

If $R_1$ in the starting material is an etherified hydroxy group, first of all addition of the thiol to the double bond occurs under basic conditions, whereupon the alcohol radical $H-R_1$ must be split off.

The alcohol $H-R_1$ is split off in the presence of an acid, in the presence or absence of a suitable inert solvent and while cooling, at room temperature or while heating, that is at temperatures between approximately −70° C. and 100° C., preferably at approximately 5° C. to approximately 40° C. Acids suitable for splitting off the alcohol $H-R_1$ are strong organic protonic acids, especially mineral acids, such as hydrochloric acid, and sulphonic acid, such as lower alkanesulphonic acids, for example methanesulphonic acid, or aromatic sulphonic acids, for example bezenesulphonic or toluenesulphonic acid, halogenated lower alkanecarboxylic acids, such as trifluoroacetic or trichloroacetic acid or also formic acid. Suitable solvents are those mentioned for the basic addition.

9. Replacement of the 3-formyl group by halogen

In a resulting compound of the formula I, in which functional groups are protected and in which $R_1$ represents a formyl group, this formyl group can be replaced by hydrogen.

The replacement of the formyl group by hydrogen is carried out by decarbonylation. This reaction is carried out especially by treating with a carbon monoxide-absorbing heavy metal complex. Examples of such heavy metal complexes are, especially, platinum metal complexes, a platinum metal meaning apart from platinum also iridium, rhodium, palladium and osmium.

Preferably bis-tri-substituted phosphine/platinum halides, bis-tri-substituted phosphine/carbonyliridium halides or tris-tri-substituted phosphine/iridium halides, especially tris-tri-substituted phosphine/rhodium halides are used, wherein the substituents of the phosphine are preferably lower alkyl, for example n-butyl, and especially phenyl, and the halides are especially chlorides. Phosphine/platinum metal complexes of this type that are capable of absorbing carbon monoxide by covalent bonding are, for example, bis-triphenylphosphine/platinum(II) chloride [$(C_6H_5)_3P]_2PtCl_2$ or bis-triphenylphosphine/carbonyliridium(II) chloride [$(C_6H_5)_3P]_2Ir(CO)Cl$, and tris-triphenylphosphine/iridium(I) chloride [$(C_6H_5)_3P]_3IrCl$, but especially tris-triphenylphosphine/rhodium(I) chloride [$(C_6H_5)_3P]_3RhCl$.

If desired or necessary, the decarbonylation with the above-mentioned heavy metal complexes can be carried out in the presence of suitable catalysts or activating agents, for example Lewis acid, such as boron trifluoride (which can be used, for example, together with the bis-triphenylphosphine/platinum chloride), or a perchlorate, such as an alkali metal perchlorate, for example sodium perchlorate (which can be used, for example, together with bis-triphenylphosphine/carbonyliridium chloride).

Preferably the process is carried out in the presence of inert solvents, especially hydrocarbons, such as aliphatic or cycloaliphatic, especially aromatic hydrocarbons, for example benzene, toluene or xylene or halogenated hydrocarbons, such as corresponding aliphatic or aromatic chlorinated hydrocarbons, for example methylene chloride or chlorobenzene; ethers, such as aliphatic, cycloaliphatic or aromatic and also mixed ethers, for example di-n-butyl ether, dioxan, diphenyl ether or anisole; nitriles, such as aliphatic or aromatic nitriles, for example acetonitrile or benzonitrile; or ketones, especially aliphatic ketones, such as lower alkanones, for example acetone, ethyl methyl ketone or isobutyl methyl ketone; or mixtures of such solvents. The reaction is carried out while cooling, at room temperature or while heating, for example at approximately 10° C. to approximately 150° C., such as at approximately 40° C. to approximately 120° C., and also, if necessary, in a closed vessel and/or in an inert gas atmosphere, for example in nitrogen or argon.

10. Conversion of $R_2$ into a different radical $R_2$

In a resulting intermediate of the formula I in which at least one of the functional groups is present in protected form, a group $R_2$ present in the radical $R_1$ may be exchanged for a different group $R_2$ as described for this reaction in the case of the end products of the formula I.

11. Methoxylation of the 7α-position

In a resulting intermediate of the formula I in which $R_3$ represents hydrogen and all the functional groups are protected, the 7α-methoxy group $R_3$ may be introduced in a manner known per se, for example by treating the said intermediate in succession with an anion-forming agent, a N-halogenating agent and methanol.

A suitable anion-forming agent is especially an organometallic base, especially an alkali metal base, especially a lithium-organic base. Compounds of this type are especially corresponding alcoholates, such as suitable lithium-lower alkanolates, especially lithium methylate, or corresponding metal hydrocarbon bases, such as lithium-lower alkanes and lithium phenyl. The reaction with the anion-forming organometallic base is usually carried out while cooling, for example from approximately 0° C. to approximately −80° C., and in the presence of a suitable solvent or diluent, for example an ether, such as tetrahydrofuran, when using lithium methylate alternatively in the presence of methanol and, if desired, in a closed vessel and/or in an inert gas atmosphere, for example a nitrogen atmosphere.

The N-halogenating agent usually used is a sterically hindered organic hypohalite, especially hypochlorite, and is especially a corresponding aliphatic hypohalite, for example hypochlorite, such as a tert.-lower alkyl hypohalite, for example a tert.-lower alkyl hypochlorite. In particular tert.-butyl hypochlorite is used, and this is reacted with the unisolated product of the anionisation reaction.

The N-halogenated intermediate is converted in the presence of an excess of the anion-forming base, especially lithium methylate, under the reaction conditions and without being isolated, into a 7-acyliminocephem compound, and this is converted into a 7α-methoxycephem compound by adding methanol. If necessary, the elements of the hydrohalic acid, especially hydrochloric acid, must be split off from the N-halogenated intermediate; this is carried out by adding a hydrohalide-splitting base, such as a suitable alkali metal lower alkanolate, for example lithium tert.-butylate, the reaction usually being carried out under the conditions of the anion-forming and N-halogen compound-forming reaction and in the presence of methanol, and instead of the ayclimino compound the 7α-methoxycephem compound can be obtained directly. The starting compound is usually a compound of the formula I in which functional groups are protected; an excess of the anion-forming agent, for example lithium methylate or phenyllithium, is reacted with this in the presence of methanol, the product is then treated with the N-halogenating agent, for example tert.-butyl hypochlorite, and in this manner the desired compound of the formula I in which functional groups are protected is obtained directly. The methanol can also be added subsequently, and the dehydrohalogenation and the addition of methanol can be carried out at slightly higher temperatures than the anion-forming and N-halogen compound-forming reactions, for example at approximately 0° C. to approximately −20° C., if necessary in a closed vessel and/or in an inert gas atmosphere, for example a nitrogen atmosphere.

In the above reactions, which are carried out under basic conditions, 3-cephem compounds may be isomerised, optionally partially, to form 2-cephem compounds. A resulting 2-cephem compound or a mixture of a 2-cephem and a 3-cephem compound may be isomerised in a manner known per se to form the desired 3-cephem compound.

MANUFACTURE OF THE STARTING COMPOUNDS

Starting compounds of the formula II and corresponding compounds with protected functional groups are known or can be produced in a manner known per se.

Compounds of the formula III in which the aminocarboxylic acid grouping $HOOC—CH(NH_2)—$ and optionally other functional groups present in the grouping A are present in protected form, are new and the invention also relates to these.

Compounds of the formula III of this type, with correspondingly protected functional groups, are produced, for example, by acylating a compound of the formula

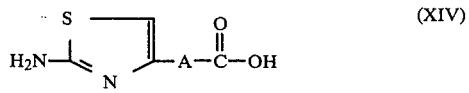

(XIV)

in which the amino group may optionally be substituted by a group allowing acylation and functional groups present in the grouping —A— are optionally protected, with the intermediate protection of the carboxyl group, with an acylating agent introducing the corresponding acyl radical of a carboxylic acid of the formula V, in which the aminocarboxylic acid grouping $HOOC—CH(NH_2)—$ is in protected form, and if desired converting a resulting compound into a different compound of the formula III with correspondingly protected functional groups.

The groups allowing acylation, and the protecting groups of the aminocarboxylic acid grouping $HOOC—CH(NH_2)—$ and the grouping A, are the same as those mentioned for the compounds of the formulae II and IV as well as I. For the intermediate protection of the carboxyl group in the compound of the formula XIV it is also possible to use the already-mentioned carboxyl-protecting groups themselves, but the carboxyl-protecting groups used for the intermediate protection in the acylation must differ from the other protecting groups that are necessarily to remain present in compounds of the formula III in the manner in which they can be split off, so that after acylation these groups can be selectively split off. If, for example, a protecting group that can be split off by hydrogenolysis is used for the intermediate protection of the carboxyl group, such as one of the mentioned optionally substituted benzyl groups, for example the benzyl or p-nitrobenzyl group, then it must not be possible for the other protecting groups to be split off by hydrogenolysis; they may be, for example, the mentioned tert.-lower alkyl groups that can be split off only by acidolysis, such as tert.-butyl, or tert.-lower alkoxycarbonyl groups, such as tert.-butoxycarbonyl.

The acylation can otherwise be carried out analogously to the acylation of compounds of the formula IV with an acid of the formula V, or a correspondingly protected and reactive functional derivative thereof.

In a resulting compound of the formula III having correspondingly protected functional groups, a protecting group can be split off optionally selectively, or a functional group optionally liberated in the acylation reaction may be protected. In a resulting compound of the formula III in which A represents hydroxymethylene, the hydroxy group may be converted into an oxomethylene group in the manner described for the oxidation of corresponding compounds I in which A is a hydroxymethylene group, for example by treating with manganese dioxide with the intermediate protection of the carboxyl group in the form of an ester, and in a resulting compound of the formula III in which A represents the oxomethylene group, this may be converted into the corresponding oxyimino group by treating with a hydroxylamine of the formula $H_2N—O—R°$, wherein this reaction may be carried out analogously to the conversion of compounds of the formula I in which A represents oxomethylene into compounds of the formula I in which A represents a corresponding oxyimino group.

Compounds of the formula IV in which the amino group may optionally be substituted by a group allowing acylation and in which the 4-carboxyl group and optionally other functional groups present in the radical $R_1$ and in the grouping —A— may be present in protected form, are in part known and in part new. They can be produced according to processes that are known per se.

New compounds of the formula IV are especially those in which A represents aminomethylene, $R_3$ represents hydrogen or methoxy and $R_1$ represents hydrogen, one of the mentioned etherified hydroxy or mercapto groups, or halogen, and their protected derivatives.

These new compounds in which the carboxyl group is optionally esterified in a form that can be split physiologically, and in which the amino groups are present in free form, and their pharmaceutically acceptable salts, likewise have an antibiotic activity. Together with the process for thier manufacture, the new compounds likewise form part of the present invention.

The mentioned new antibiotically active compounds of the formula IV may be used as anti-bacterial antibiotics. They are effective against a series of pathogenic microorganisms, especially gram-positive and gram-negative bacteria, such as *Staphylococcus aureus*, including resistant strains of staphylococcus, *Escherichia coli* and *Proteus vulgaris* (for example, inhibiting zones of approximately 11 to 30 mm are ascertained in the plate test against the bacteria mentioned), and can therefore be used accordingly, for example in the form of antibiotically active preparations, for the treatment of infections caused by such micro-organisms. These compounds are especially also active orally.

Preferred are such compounds of the formula IV in which A represents aminomethylene, especially in the D-form, $R_1$ represents hydrogen, methoxy or chlorine, and $R_3$ represents hydrogen, and pharmaceutically acceptable salts thereof.

Compounds of the formula IV in which the amino group and the other functional groups may optionally be protected or substituted as stated, and their salts, may be produced analogously to the compounds I, for example by acylating a compound of the formula II, in which the amino group is optionally substituted by a group allowing acylation and in which the 4-carboxyl group and optionally other functional groups present in the radical $R_1$ may be present in protected form, with an acylating agent introducing the acyl radical of an acid of the formula XIV, wherein the amino group may optionally be protected and functional groups present in the grouping —A— are optionally protected, for example with a reactive functional derivative of such an acid or a salt thereof, if desired splitting off the protecting groups in a resulting compound and/or, if desired, converting a resulting compound in which $R_3$ represents hydrogen into a compound in which $R_3$ represents methoxy, and/or, if necessary, isomerising a resulting 2-cephem compound or a resulting mixture of a 2-cephem and a 3-cephem compound to form the 3-cephem compound and/or, if desired, separating a resulting isomeric mixture into the isomers, and/or, if desired, converting a resulting compound with a salt-forming group into a salt or a resulting salt into the free compound.

The groups in the compounds of the formula II that allow acylation and the protecting groups are the same as those already mentioned above.

The acylation of corresponding protected compounds of the formula II, the splitting off of the protecting groups and the introduction of the methoxy group $R_3$, as well as the salt formation, can be carried out in the same manner as described for the acylation of correspondingly protected compounds of the formula II or IV with an acid of the formula III or V, respectively, and the corresponding subsequent operations.

Acids of the formula V, reactive functional derivatives thereof, the preliminary substances of the formula HOOC—CH(NH$_2$)—(C$_n$H$_{2n}$)—X—H (VI) and correspondingly protected derivatives are known or may be produced according to methods known per se, for example in situ.

Reactive functional derivatives of acids of the formula VII in which the 4-carboxyl group and optionally functional groups present in the radical $R_1$ and in the grouping —A— may be present in protected form, are produced in a manner known per se from correspondingly protected compounds of the formula IV.

Acids of the formula XIV and corresponding reactive functional and protected derivatives thereof are known or may be produced in accordance with methods known per se.

Starting compounds of the formula VIII are known or may be produced in a manner known per se, for example by acylation of compounds of the formula II, and optionally corresponding subsequent operations.

Starting compounds of the formula IX in which functional groups, especially the aminocarboxylic acid grouping, are optionally protected, are new. They may be produced, for example, by treating a compound of the formula VI, in which the aminocarboxylic acid grouping is present in protected form, with phosgene or thiophosgene in the presence of a base, treating the resulting acid chloride of a compound of the formula V with a salt of thiocyanic acid, for example with an alkali metal thiocyanide, such as potassium thiocyanide, and treating the resulting compound of the formula

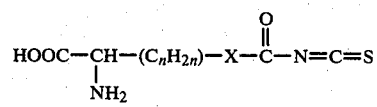

with ammonia.

Starting compounds of the formula X in which $R_1{}^a$ is an optionally esterified hydroxy group, fall under the compounds of the formula I with corresponding protected groups, and can accordingly be produced as described for these compounds.

Starting compounds of the formula X, in which $R_1{}^a$ is a secondary or tertiary amino group —N($R_4{}^a$)($R_4{}^b$), may be obtained from compounds of the formula X in which $R_1{}^a$ is an optionally esterified hydroxy group, by reacting with an amine of the formula HN($R_4{}^a$)($R_4{}^b$), or by using as starting materials compounds of the formulae II, IV, VII, VIII, XII or XIII, in which $R_1$ represents a secondary or tertiary amino group —N($R_4{}^a$)($R_4{}^b$), optionally with the protection of groups not participating in the reactions, in a manner analogous to the processes (a), (b), (c), (d), (f) and (g).

The cepham compounds optionally formed as intermediates in process (e) may be produced analogously to the acylation and condensation processes (a) to (d), using as starting materials known cepham compounds or cepham compounds that can be produced in a manner known per se having the formula

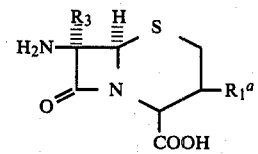

Starting compounds of the formula XI with protected functional groups may be produced in a manner known per se, for example analogously to DT-OS No. 2 151

567, in which in the last step a corresponding hydroxy compound of the partial formula —S—CH₂CH₂—OH is oxidised to form the carbonyl compound of the formula XI.

The oxidation can be carried out by treating with an oxidising organic sulphoxide compound in the presence of agents having water-removing or water-absorbing properties. Suitable oxidising sulphoxide compounds are especially aliphatic sulphoxide compounds, such as di-lower alkyl sulphoxides, especially dimethyl sulphoxide, or lower alkylene sulphoxides, for example tetramethylene sulphoxide. Examples of agents having water-removing or water-absorbing properties are especially acid anhydrides, especially anhydrides of organic, such as aliphatic or aromatic, carboxylic acids, for example anhydrides of lower alkane-carboxylic acids, especially acetic acid anhydride, also propionic acid anhydride, or benzoic acid anhydride, and anhydrides of inorganic acids, especially of phosphoric acids, such as phosphorus pentoxide. The above anhydrides, especially of organic carboxylic acids, for example acetic acid anhydride, are preferably used in an approximately 1:1 mixture with the sulphoxide oxidising agent. Other water-removing or water-absorbing agents are carbodiimides, especially dicyclohexylcarbodiimide, and also diisopropylcarboxiimide, or ketenimines, for example diphenyl-N-p-tolylketenimine; these reagents are preferably used in the presence of acidic catalysts, such as phosphoric acid or pyridinium trifluoroacetate or trifluorophosphate. Sulphur trioxide may likewise be used as water-removing or water-absorbing agent, wherein it is usually used in the form of a complex, for example with pyridine.

Usually, the sulphoxide oxidising agent is used in excess. Sulphoxide compounds liquid under the reaction conditions, especially dimethyl sulphoxide, may, for example, simultaneously be used as solvents; in addition it is possible to use as solvents inert diluents, such as optionally halogenated hydrocarbons, preferably of aliphatic or aromatic character, for example benzene, or mixtures of solvents.

The above oxidation is, if desired, carried out while cooling, but mostly at room temperature or slightly elevated temperature, for example at temperatures of approximately −20° C. to approximately 100° C.

Starting compounds of the formula XII with protected functional groups, may be produced in a manner known per se, for example analogously to DT-OS No. 2 506 330 or Belgian Pat. Nos. 838 656 or 844 344.

2-Cephem starting compounds of the formula XIII are new. They may be produced analogously to the acylating and condensing processes (a) to (d) using as starting materials known 2-cephem compounds or 2-cephem compounds that can be produced in a manner known per se of the formula

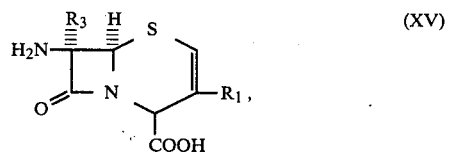

They may furthermore be produced as side-products in the processes (a) to (e), especially when basic conditions are applied.

The pharmacologically acceptable compounds of the present invention can be used, for example, for the manufacture of pharmaceutical preparations that contain an active amount of the active substance together or in admixture with inorganic or organic, solid or liquid, pharmaceutically acceptable carriers that are suitable preferably for parenteral administration.

Preferably, the pharmacologically active compounds of the present invention are used in the form of injectable, for example intravenously, administrable preparations or of infusion solutions. Solutions of this type are preferably isotonic aqueous solutions or suspensions, and these can be produced, for example, from lyophilised preparations that contain the active substance alone or together with a carrier, for example mannitol, before use. The pharmaceutical preparations may be sterilised and/or may contain auxiliaries, for example preservatives, stabilisers, wetting agents and/or emulsifiers, solubilisers, salts for regulating the osmotic pressure and/or buffers. The present pharmaceutical preparations which, if desired, may contain other pharmacologically valuable substances, are produced in a manner known per se, for example by means of conventional dissolving or lyophilising processes, and contain from approximately 0.1% to 100%, especially from approximately 1% to approximately 50%, or, in the case of lyophilisates, up to 100%, of the active substance. Depending on the nature of the infection and the state of the infected organism, daily dosages of approximately 0.5 g to approximately 5 g s.c. are used for treating warm-blooded animals to approximately 70 kg weight.

The antibiotically active compounds of the formula IV may also be administered orally, for example in the form of customary orally-administrable, pharmaceutical preparations, such as tablets, capsules or solutions, that contain an active amount of the compound and optionally a customary acceptable pharmaceutical additive.

The following Examples illustrate the invention; temperatures are given in degrees Centigrade.

The following abbreviations are used in the Examples:
BOC: tert.-butoxycarbonyl
M.p.: melting point
TLC: thin layer chromatogram on silica gel ready-made plates SL 254, produced by Messrs. Antec, Birsfelden;
$RF_{96}$: Rf value in the solvent system sec. butanol/glacial acetic acid/water 67:10:23.

EXAMPLE 1

Sodium 7β-{2-[2-((2R)-2-amino-2-carboxyethoxycarbonylamino)thiazol-4-yl]acetylamino}-3-acetoxymethyl-3-cephem-4-carboxylate trihydrate (a) 35 ml of cold trifluoroacetic acid are added to a solution, cooled to 0°, of 7 g (8.6 mmoles) of 7β-{2-[2-((2R)-2-BOC-amino-2-diphenylmethoxycarbonylethoxycarbonylamino)thiazol-4-yl]acetylamino}-3-acetoxymethyl-3-cephem-4-carboxylic acid and 7 ml of anisole in methylene chloride (35 ml) and the mixture is stirred for 30 minutes at 0° under a nitrogen atmosphere and in the absence of moisture. After adding diethyl ether (700 ml) the trifluoroacetate of the title compound, which is obtained in crystalline form, is filtered off, washed with diethyl ether and dried in a high vacuum at room temperature. The aqueous solution (40 ml) of the crude trifluoroacetate is adjusted to a pH of 6 with concentrated sodium bicarbonate solution, extracted with ethyl acetate (2×20 ml) and acetone (200 ml) is added. The precipitate formed is filtered off, washed with acetone, dissolved in a little water and concentrated in a rotary evaporator twice and, after drying in a high volume, the title compound is obtained in the form of an amorphous powder.

$[\alpha]_D = +86° \pm 1°$ (c=1.127%, H$_2$O)

TLC: Rf$_{96}$=0.17.

The starting materials can be obtained as follows:

(b) A suspension of 100 g of (2R)-serine in 1 l of water is dissolved by adding slowly 100 g of solid, anhydrous sodium carbonate, then 2 l of dioxan and 346 g of di-tert.-butyl pyrocarbonate are added and the mixture is stirred for 30 minutes at 20°. The dioxan is evaporated off in vacuo and the aqueous phase is extracted at 0° and a pH of 2.0 with ethyl acetate. 236.7 g of amorphous, crude (2R)-N-BOC-serine containing approximately 195 g of pure product are obtained. By triturating with petroleum ether and cooling, the pure compound can be obtained; m.p. 78°–83° (decomposition).

(c) A solution of approximately 214 g of diphenyldiazomethane in 1 l of methylene chloride is added dropwise at 22°, while cooling, to a solution of 236.7 g of the resulting crude (2R)-BOC-serine in 700 ml of methylene chloride and the mixture is stirred for 1½ hours at 20°. The mixture is concentrated by evaporation in vacuo, the residue is taken up in ethyl acetate and washed at 0° with a phosphate buffer of a pH of 2.0 then of a pH of 7.0. The dried organic phase yields a crystalline residue on concentration by evaporation which is digested in hexane and, after filtering, (2R)-N-BOC-serine diphenylmethyl ester is obtained; m.p. 116°–117° (corrected).

$[\alpha]_D^{20} = +6° \pm 1°$ (c=1, chloroform).

(d) 4.9 ml of N,O-bis-(trimethylsilyl)acetamide are added at room temperature and under a nitrogen atmosphere to a solution of 4.536 g (11 mmoles) of 7β-[2-(2-aminothiazol-4-yl)acetylamino]-3-acetoxymethyl-3-cephem-4-carboxylic acid in 100 ml of absolute methylene chloride and the mixture is stirred for one hour (solution A). 3.71 g (10 mmoles) of (2R)-N-BOC-serine diphenylmethyl ester dissolved in 70 ml of absolute methylene chloride, then 0.85 ml (10.5 mmoles) of absolute pyridine, are added dropwise to a solution, cooled to 0°, of phosgene in toluene (5.2 ml; 20% by weight) diluted with 30 ml of methylene chloride, and the mixture is stirred for one hour at 0° under a nitrogen atmosphere (solution B). Solution A, and then 0.85 ml (10 mmoles) of absolute pyridine, are added to solution B at 0° while stirring. The reaction mixture is stirred for 30 minutes at 0° and for 2 hours at room temperature, diluted with ethyl acetate (800 ml), washed with water (3×50 ml) and saturated sodium chloride solution (50 ml) and dried over sodium sulphate and the solvent is removed in a rotary evaporator. The residue contains the 7β-{2-[2-((2R)-2-BOC-amino-2-diphenylmethoxycarbonylethoxycarbonylamino)thiazol-4-yl]-acetylamino}-3-acetoxymethyl-3-cephem-4-carboxylic acid in the form of an amorphous yellow powder.

TLC: Rf$_{96}$=0.59

The compound obtainable according to Example (d) can also be produced as follows:

(e) 3.71 g (10 mmoles) of (2R)-N-BOC-serine diphenylmethyl ester and 0.8 l of absolute pyridine dissolved in 40 ml of absolute tetrahydrofuran are added in the course of approximately 15 minutes, while stirring and in the absence of moisture, to a solution, cooled to −20° C., of 5.4 ml (11 mmoles) of phosgene in toluene (20% by weight) diluted with 10 ml of absolute tetrahydrofuran. After 15 minutes the precipitate (pyridine hydrochloride) is filtered off at 0° and the filtrate is added to a solution of 1.07 g (11 moles) of potassium thiocyanate in 20 ml of absolute acetone at −10°. After 30 minutes 4.4 ml of 2.5 molar methanolic ammonia solution are added to the reaction mixture, the mixture is brought to room temperature in the course of one hour and then the solvent is removed in a rotary evaporator. The residue, dissolved in ethyl acetate (100 ml), is washed with water (2×20 ml), dried over sodium sulphate and concentrated. The crude product is purified over 25 times the amount of silica gel with chloroform/acetone (9:1) as eluant, and from this, after crystallisation from diethyl ether, N-((2R)-2-BOC-amino-2-diphenylmethoxycarbonylethoxycarbonyl)thiourea is obtained in the form of a colourless crystallisate having a melting point of 145°–147°.

TLC: Rf=0.34 (eluant: chloroform/acetone 9:1).

(f) A solution of a 391 mg (1.0 mmole) of 7β-(4-chloro-3-oxobutyramido)cephalosporanic acid, 84 mg (1.0 mmole) of sodium bicarbonate and 521 mg (1.1 mmole) of N-((2-R)-2-BOC-amino-2-diphenylmethoxycarbonylethoxycarbonyl) thiourea in 5 ml of absolute ethanol is stirred for 5 hours at 70° C. in a nitrogen atmosphere. After removing the solvent the residue is dissolved in ethyl acetate (approximately 20 ml) and washed twice with dilute hydrochloric acid (pH 2). After drying the organic phase with sodium sulphate and removing the solvent in a rotary evaporator, the crude product is purified over silica gel with methylene chloride/ethyl acetate (2:1). The resulting 7β-{2-[2-((2R)-2-BOC-amino-2-diphenylmethoxycarbonylethoxycarbonylamino)thiazol-4-yl]acetylamino}-3-acetoxymethyl-3-cephem-4-carboxylic acid is identical to the compound produced in accordance with Example 1(d).

EXAMPLE 2

Sodium 7β-{2-[2-((2R)-2-amino-2-carboxyethoxycarbonylamino)thiazol-4-yl]-2-syn-methoxyiminoacetylamino}-3-acetoxymethyl-3-cephem-4-carboxylate (a) 23 ml of trifluoroacetic acid are added to a solution, cooled to 0°, of 4.5 g of 7β-{2-[2-((2R)-2-BOC-amino-2-diphenylmethoxycarbonylethoxycarbonylamino)thiazol-4-yl]-2-syn-methoxyiminoacetylamino}-3-acetoxymethyl-3-cephem-4-carboxylic acid and 4.5 ml of anisole in absolute methylene chloride (23 ml) and the mixture is stirred for 30 minutes at 0° in a nitrogen atmosphere and in the absence of moisture. After adding diethyl ether (300 ml), the trifluoroacetate of the title compound, obtained in crystalline form, is filtered off, washed with diethyl ether and dried in a high vacuum at room temperature. The aqueous solution (20 ml) of the resulting crude trifluoroacetate (pH~2) is adjusted to a pH of 7 with saturated sodium bicarbonate solution and chromatographed over Amberlite XAD-2 with water/isopropanol (12:88) as eluant. The thin layer chlomatographically uniform fractions are combined and concentrated in a rotary evaporator, and the residue is crystallised from 70 ml of water/isopropanol (1:4) and, after filtering, dried in a high vacuum at room temperature. The title compound is obtained in the form of a pale yellow crystallisation product with 1.6 mole of water of crystallisation.

M.p. from 170° (decomposition);

$[\alpha]_D = +50° \pm 1°$ (c=1.024%, H$_2$O);

TLC: $Rf_{96}=0.14$.

The starting materials may be obtained as follows:

(b) 21.5 g (0.1 mole) of 2-(2-aminothiazol-4-yl)-2-syn-methoxyiminoacetic acid methyl ester dissolved in 900 ml of ethanol are added, while stirring, to a solution of 28 g of potassium hydroxide in 160 ml of water. The reaction mixture is stirred for 3 hours at room temperature. After removing the solvent, the residue is dissolved in 200 ml of water and extracted with ethyl acetate (3×100 ml). The aqueous phase, cooled to 0°, is adjusted to a pH of 3 with 2 N hydrochloric acid and is further stirred for approximately 1 hour. The precipitate formed is filtered off, washed with a little ice-water and acetone and dried in a high vacuum at room temperature. 2-(2-aminothiazol-4-yl)-2-syn-methoxyiminoacetic acid is thus isolated in the form of an inner salt.

M.p. 119°-122° (decomposition);

TLC: $Rf_{96}=0.14$.

(c) 1 ml of absolute pyridine, then 4.45 g (12 mmoles) of (2R)-N-BOC-serine diphenylmethyl ester dissolved in 20 ml of methylene chloride, are added dropwise, while stirring and in the absence of moisture, to a solution, cooled to 0°, of 20.4 ml of phosgene in toluene (20% by weight), diluted with 20 ml of methylene chloride and the mixture is stirred for one hour at 0° C. The suspension (precipitate of pyridine hydrochloride) is diluted with methylene chloride (150 ml) and washed with ice water (3×30 ml) and the organic phase is dried over sodium sulphate. After removing the solvent in a rotary evaporator, the oily crude product is stirred well with petroleum ether and, after filtration and drying in a high vacuum, (2R)-2-BOC-amino-2-diphenylmethoxycarbonylethoxycarbonyl chloride is obtained in crystalline form.

M.p. 78°-80° (decomposition).

(d) 9.7 of N,O-bis-(trimethylsilyl)acetamide are added, while stirring and in the absence of moisture, to a suspension of 4.02 g (0.02 mole) of 2-(2-aminothiazol-4-yl)-2-syn-methoxyiminoacetic acid in 100 ml of absolute tetrahydrofuran and the mixture is allowed to react for one hour at room temperature. 8.67 g (0.02 mole) of (2R)-2-BOC-amino-2-diphenylmethoxycarbonylethoxycarbonyl chloride dissolved in 100 ml of absolute tetrahydrofuran are added dropwise in the course of approximately 10 minutes to the silylated acetic acid, which has been cooled to 0°, and then 1.6 ml of absolute pyridine are added. After a reaction time of 1 hour at 0°, and 2 hours at room temperature, the solvent is removed in a rotary evaporator and the oily residue is dissolved in 200 ml of cold 0.5 M sodium bicarbonate solution and extracted with diethyl ether (2×100 ml). Ethyl acetate (400 ml) is poured onto the aqueous phase, the pH is adjusted to 2 with 2 N hydrochloric acid and, after separating the organic phase, the mixture is extracted twice more with ethyl acetate (200 ml). The combined organic phases are washed with saturated sodium chloride solution and dried over sodium sulphate and the solvent is removed in a rotary evaporator. 2-[2-((2R)-BOC-amino-2-diphenylmethoxycarbonylethoxycarbonylamino)thiazol-4-yl]-2-syn-methoxyiminoacetic acid is isolated in amorphous form.

TLC: $Rf_{96}=0.65$.

(e) 2.27 g (11 mmoles) of N,N'-dicyclohexylcarbodiimide dissolved in 20 ml of absolute tetrahydrofuran are added dropwise to a solution, cooled to 0°, of 5.98 g (10 mmoles) of 2-[2-((2R)-BOC-amino-2-diphenylmethoxycarbonylethoxycarbonylamino)thiazol-4-yl]-2-syn-methoxyiminoacetic acid and 1.35 g (10 mmoles) of 1-hydroxybenztriazole (moistened with 10% water) in 60 ml of absolute tetrahydrofuran and the reaction mixture is stirred for 2 hours at 0°. A solution of 4.38 g (10 mmoles) of 7β-amino-3-acetoxymethyl-3-cephem-4-carboxylic acid diphenylmethyl ester in 40 ml of tetrahydrofuran is added dropwise to the yellow suspension. After 4 hours at 0°, the resulting precipitate (N,N'-dicyclohexyl urea) is suction-filtered, the filtrate is concentrated in a rotary evaporator, the residue is dissolved in diethyl ether (300 ml), washed three times with dilute sodium bicarbonate solution and water and dried over sodium sulphate, and the solvent is removed in a rotary evaporator. The crude product is purified over 50 times the amount of silica gel using diethyl ether as eluant. The thin layer chromatographically uniform fractions of 7β-{2-[2-((2R)-2-BOC-amino-2-diphenylmethoxycarbonylethoxycarbonylamino)thiazol-4-yl]-2-syn-methoxyiminoacetylamino}-3-acetoxymethyl-3-cephem-4-carboxylic acid diphenylmethyl ester are combined and used directly in the next synthesising step.

TLC: $Rf=0.26$ (eluant: diethyl ether).

EXAMPLE 3

Sodium 7β-{2-[2-((2R)-amino-2-carboxyethoxycarbonylamino)-thiazole-4-yl]-2-syn-methoxyiminoacetylamino}-3-carbamoyloxymethyl-3-cephem-4-carboxylate trihydrate (a) In a manner analogous to that described in Example 2(a), by treating 2.5 g (2.5 mmoles) of 7β-{2-[2-((2R)-2-BOC-amino-2-diphenylmethoxycarbonylethoxycarbonylamino)thiazol-4-yl]-2-syn-methoxyiminoacetylamino}-3-carbamoyloxy-3-cephem-4-carboxylic acid diphenylmethyl ester with 12.5 ml of trifluoroacetic acid in the presence of 2.5 ml of anisole in 12.5 ml of absolute methylene chloride, the amino group and the protected carboxyl groups are liberated, the resulting trifluoroacetic acid salt is adjusted to a pH of 7 by treating with saturated sodium bicarbonate solution in water and, after chromatography over Amberlite XAD-2, the title compound is obtained.

M.p. from 210° (decomposition);

$[\alpha]_D = +46° \pm 1°$ (c=1.416%, $H_2O$);

TLC: $Rf_{96}=0.14$.

The starting material can be produced as follows:

(b) In a manner analogous to that described in Example 2(e), by treating the activated ester (produced from 2.99 g (5 mmoles) of 2-[2-((2R)-2-BOC-amino-2-diphenylmethoxycarbonylethoxycarbonylamino)-thiazole-4-yl]-2-syn-methoxyiminoacetic acid and 0.743 g (5 mmoles) of 1-hydroxybenztriazole in the presence of 1.13 g (5.5 mmoles) of N,N'-dichlorohexylcarbodiimide in 40 ml of tetrahydrofuran at 0° for 2 hours) with 1.98 g (4.5 mmoles) of 7β-amino-3-carbamoyloxymethyl-3-cephem-4-carboxylic acid diphenylmethyl ester dissolved in 20 ml of tetrahydrofuran, 7β-{2-[2-((2R)-2-BOC-amino-2-diphenylmethoxycarbonylethoxycarbonylamino)thiazol-4-yl]-2-syn-methoxyiminoacetylamino}-3-carbamoyloxy-3-cephem-4-carboxylic acid diphenylmethyl ester is obtained which, after chromatographic purification over silica gel with diethyl ether/ethyl acetate (1:1) as eluant, is used in the next synthesising step.

TLC: $Rf=0.57$ (eluant: ethyl acetate);

Infra-red spectrum in methylene chloride: characteristic bands at 3400, 1785, 1730 and 1685 $cm^{-1}$.

EXAMPLE 4

Sodium 7β-{2-[2-((2R)-2-amino-2-carboxyethoxycarbonylamino)thiazol-4-yl]-2-syn-methoxyiminoacetylamino}-3-methoxy-3-cephem-4-carboxylate dihydrate (a) In a manner analogous to that described in Example 2(a), by treating 2.93 g (3 mmoles) of 7β-{2-[2-((2R)-2-BOC-amino-2-diphenylmethoxycarbonylethoxycarbonylamino)thiazol-4-yl]-2-syn-methoxyiminoacetylamino}-3-methoxy-3-cephem-4-carboxylic acid diphenylmethyl ester with 15 ml of trifluoroacetic acid in the presene of 3 ml of anisole in 15 ml of methylene chloride, the amino group and the protected carboxyl groups are liberated, the resulting trifluoroacetic acid salt is adjusted to a pH of 7 by treating with 10% sodium bicarbonate solution in 15 ml of water and, by the subsequent addition of isopropanol (80 ml), the title compound is obtained.

M.p. 176°–179° (decomposition);
$[\alpha]_D^{20} = +96° \pm 1°$ (c=1.044, $H_2O$);
TLC: $Rf_{96}=0.12$.

The starting material can be obtained as follows:

(b) In a manner analogous to that described in Example 2(e), by treating the activated ester (produced from 2.99 g (5 mmoles) of 2-[2-((2R)-2-BOC-amino-2-diphenylmethoxycarbonylethoxycarbonylamino)-thiazol-4-yl]-2-synmethoxyiminoacetic acid and 0.743 g (5 mmoles) of 1-hydroxybenztriazole in the presence of 1.13 g (5.5 mmoles) of N,N'-dicyclohexylcarbodiimide in 45 ml of tetrahydrofuran at 0° for 2 hours) with 2.17 g (5 mmoles) of 7β-amino-3-methoxy-3-cephem-4-carboxylic acid diphenylmethyl ester hydrochloride dissolved in 20 ml of tetrahydrofuran, and then with 0.56 ml (5 mmoles) of N-methylmorpholine, 7β-{2-[2-((2R)-2-BOC-amino-2-diphenylmethoxycarbonylethoxycarbonylamino)thiazol-4-yl]-2-syn-methoxyiminoacetylamino}-3-methoxy-3-cephem-4-carboxylic acid diphenylmethyl ester is obtained which, after chromatographic purification over silica gel with diethyl ether/ethyl acetate (1:1) as eluant, is used in the next synthesising step.

TLC: Rf=0.47 (eluant: diethyl ether/ethyl acetate 1:1).

EXAMPLE 5

Sodium 7β-{2-[2-((2R)-2-amino-2-carboxyethoxycarbonylamino)thiazol-4-yl]-2-syn-methoxyiminoacetylamino}-3-[(1-methyl-1H-tetrazol-5-yl)thiomethyl]-3-cephem-4-carboxylate dihydrate (a) In a manner analogous to that described in Example 2(a), by treating 2.65 g (2.47 mmoles) of 7β-{2-[2-((2R)-2-BOC-amino-2-diphenylmethoxycarbonylethoxycarbonylamino)thiazol-4-yl]-2-syn-methoxyiminoacetylamino}-3-[(1-methyl-1H-tetrazol-5-yl)thiomethyl]-3-cephem-4-carboxylic acid diphenylmethyl ester with 13 ml of trifluoroacetic acid in the presence of 2.6 ml of anisole in 13 ml of methylene chloride, the amino group and the protected carboxyl groups are liberated, the resulting trifluoroacetate salt, dissolved in 15 ml of water, is adjusted to a pH of 7 by adding 10% sodium bicarbonate solution and the title compound is obtained by adding isopropanol (80 ml).

M.p. from 150° (decomposition);
$[\alpha]_D = -17° \pm 1°$ (c=0.92%, $H_2O$);
TLC: $Rf_{96}=0.13$.

The starting material can be produced as follows:

(b) In a manner analogous to that described in Example 2(e), by treating the activated ester (produced from 2.99 g (5 mmoles) of 2-[2-((2R)-2-BOC-amino-2-diphenylmethoxycarbonylethoxycarbonylamino)-thiazol-4-yl]-2-syn-methoxyiminoacetic acid and 0.743 g (5 mmoles) of 1-hydroxybenztriazole in the presence of 1.13 g (5.5 mmoles) of N,N'-dicyclohexylcarbodiimide in 45 ml of tetrahydrofuran at 0° for 2 hours) with 2.47 g (5 mmoles) of 7β-amino-3-[(1-methyl-1H-tetrazol-5-yl)]thiomethyl-3-cephem-4-carboxylic acid diphenylmethyl ester, 7β-{2-[2-((2R)-2-BOC-amino-2-diphenylmethoxycarbonylethoxycarbonylamino)thiazol-4-yl]-2-syn-methoxyiminoacetylamino}-3-[(1-methyl-1H-tetrazol-5-yl)thiomethyl]-3-cephem-4-carboxylic acid diphenylmethyl ester is obtained which, after chromatographic purification over silica gel with diethyl ether/ethyl acetate (1:1) as eluant, is used in the next synthesising step.

TLC: Rf=0.59 (eluant: diethyl ether/ethyl acetate 1:1).

EXAMPLE 6

7β-{(2R,S)-2-[2-((2R)-2-amino-2-carboxyethoxycarbonylamino)thiazol-4-yl]-2-aminoacetylamino}-3-methoxy-3-cephem-4-carboxylic acid (a) 21 ml of trifluoroacetic acid are added to a solution, cooled to 0°, of 2.1 g (2 mmoles) of 7β-{(2R,S)-2-[2-((2R)-2-BOC-amino-2-diphenylmethoxycarbonylethoxycarbonylamino)thiazol-4-yl]-2-BOC-aminoacetylamino}-3-methoxy-3-cephem-4-carboxylic acid diphenylmethyl ester and 4.2 ml of anisole in absolute methylene chloride (21 ml) and the mixture is stirred for one hour at 0° under a nitrogen atmosphere and in the absence of moisture. After adding diethyl ether (210 ml) the trifluoroacetate, produced in crystalline form, is filtered off, washed with diethyl ether and dried in a high vacuum at room temperature.

The aqueous solution (10 ml) of the crude trifluoroacetate (pH 1.8) is extracted with ethyl acetate (2×5 ml) and the pH is adjusted to 5 with 1 N sodium hydroxide solution. By adding isopropanol the title compound is obtained in microcrystalline form.

TLC: $Rf_{96}=0.11$.

The starting material can be produced as follows:

(b) A solution of 64 ml of 2,2,2-trichloroethoxycarbonyl chloride in 150 ml of absolute tetrahydrofuran is added in the course of approximately 30 minutes to a solution, cooled to 0°, of 64.5 g (0.3 mole) of 2-(2-aminothiazol-4-yl)-2-syn-methoxyiminoacetic acid methyl ester and 42 ml of absolute pyridine in 600 ml of absolute dimethylformamide while stirring and in the absence of moisture. After 2 hours at 0°, the reaction mixture is diluted with diethyl ether (1800 ml), and the precipitated pyridine hydrochloride is filtered off and washed with water (4×300 ml). The organic phase is dried over sodium sulphate and concentrated in a rotary evaporator. The crude product is then purified over 10 times the amount of silica gel with hexane/diethyl ether (1:1)an eluant and, after crystallisation from diethyl ether/petroleum ether (1:1), 2-[2-(2,2,2-trichloroethoxycarbonylamino)thiazol-4-yl]-2-syn-methoxyiminoacetic acid methyl ester is isolated.

M.p. 105°–107°;
TLC: Rf=0.48 (eluant: hexane/diethyl ether 1:1).

(c) A solution of 38.0 g (97 mmoles) of 2-[2,2,2-trichloroethoxycarbonylamino)thiazol-4-yl]-2-methoxyiminoacetic acid methyl ester in 1000 ml of methyl alcohol, which contains 9% hydrogen chloride, is hydrogenated in the presence of 38 g of 10% palladium/carbon at room temperature. After absorption of the theoretical amount of hydrogen, the reaction mixture is filtered through Celite and concentrated in a rotary evaporator. The residue is washed with diethyl ether, suspended in ethyl acetate (800 ml), and washed with 5% sodium bicarbonate solution (2×200 ml) and water. The organic phase is dried ($Na_2SO_4$) and concentrated and (2R,S)-2-[2-(2,2,2-trichloroethoxycarbonylamino)-thiazol-4-yl]-2-aminoacetic acid methyl ester is obtained in the form of a light yellow oil.

TLC: $Rf_{96}=0.48$.

(d) 17.2 g of potassium hydroxide dissolved in 172 ml of water are added to a solution of 23.0 g (57.5 mmoles) of (2R,S)-2-[2-(2,2,2-trichloroethoxycarbonylamino-thiazol-4-yl]-2-aminoacetic acid methyl ester in 940 ml of ethanol and the mixture is stirred for two hours at room temperature. The reaction mixture is concentrated to approximately 100 ml, diluted with 250 ml of water, extracted with ethyl acetate (2×100 ml) and the aqueous phase, cooled to 0°, is adjusted to a pH of 4 with 2 N hydrochloric acid. After one hour, the colourless, crystalline (2R,S)-2-[2-(2,2,2-trichloroethoxycarbonylamino)thiazol-4-yl]-2-aminoacetic acid is filtered off, washed with a little water and dried in a high vacuum (16 hours, 0.05 torr, room temperature, $P_2O_5$).

M.p. from 160° (decomposition);

TLC: $Rf_{96}=0.45$.

(e) 4.06 g of di-tert.-butyl dicarbonate are added in one portion, at room temperature, to a well-stirred suspension of 6.07 g (17 mmoles) of (2R,S)-2-[2-(2,2,2-trichloroethoxycarbonylamino)thiazol-4-yl]-b 2-aminoacetic acid and 1.794 g (~17 mmoles) of sodium carbonate in 70 ml of water/dioxan (1:2). After two hours, after adding 50 ml of water at 0°, the reaction mixture is adjusted to a pH of 2 with 2 N hydrochloric acid and extracted with ethyl acetate (3×250 ml). The combined organic phases are dried ($Na_2SO_4$) and concentrated. The crude product is purified over 30 times the amount of silica gel using diethyl ether as eluant. After crystallisation from diethyl ether, (2R,S)-2-[2-(2,2,2-trichloroethoxycarbonylamino)thiazol-4-yl]-2-BOC-aminoacetic acid is isolated in the form of colourless crystals.

M.p. 183°–184°;

TLC: $Rf_{96}=0.78$.

(f) 1.3 ml (10 mmoles) of chloroformic acid isobutyl ester are added under a nitrogen atmosphere and in the absence of moisture to a solution, cooled to −20°, of 4.48 g (10 mmoles) of (2R,S)-2-[2-(2,2,2-trichloroethoxycarbonylamino)thiazol-4-yl]-2-BOC-aminoacetic acid and 1.12 ml of N-methylmorpholine in 100 ml of absolute methylene chloride. After 40 minutes at −20° the resulting mixed anhydride is reacted in one portion with 4.33 g (10 mmoles) of 7β-amino-3-methoxy-3-cephem-4-carboxylic acid diphenylmethyl ester hydrochloride, followed by 1.12 ml of N-methylmorpholine. After a reaction time of 30 minutes at 0° and 2 hours at room temperature, the reaction mixture is diluted with ethyl acetate (400 ml) and washed with water (2×100 ml) and concentrated sodium chloride solution. After drying ($Na_2SO_4$) the organic phase and removing the solvent in a rotary evaporator, the resulting crude product is purified over 30 times the amount of silica gel with diethyl ether as eluant, and 7β-{(2R,S)-2-[2-(2,2,2-trichloroethoxycarbonylamino)thiazol-4-yl]-2-BOC-aminoacetylamino}-3-methoxy-3-cephem-4-carboxylic acid diphenylmethyl ester is obtained in the form of a colourless powder.

TLC: Rf=0.63 (eluant: diethyl ether/ethyl acetate 1:1);

Infra-red spectrum in methylene chloride: chracteristic bands at 3400, 1780, 1750, 1715, 1695, 1550 and 1210 $cm^{-1}$.

(g) 8 g of zinc dust are added in portions, while stirring vigorously, to a solution, cooled to 0°, of 8 g (1.67 mmoles) of 7β-{(2R,S)-2-[2-(2,2,2-trichloroethoxycarbonylamino)thiazol-4-yl]-2-BOC-aminoacetylamino}-3-methoxy-3-cephem-4-carboxylic acid diphenylmethyl ester in 80 ml of acetonitrile/acetic acid (1:1). After one hour the zinc is filtered off, washed with acetonitrile and the filtrate concentrated. The residue is taken up in ethyl acetate (400 ml) and washed with 1 N sodium bicarbonate solution (2×80 ml) and saturated sodium chloride solution. After drying the organic phase over sodium sulphate, the solvent is removed in a rotary evaporator and 7β-[(2R,S)-2-(2-aminothiazol-4-yl)-2-BOC-aminoacetylamino]-3-methoxy-3-cephem-4-carboxylic acid diphenylmethyl ester is obtained which can be used in the next synthesising step without further purification.

TLC: Rf=0.69 (eluant: ethyl acetate);

Infra-red spectrum in methylene chloride: characteristic bands at 3380, 3300, 1782, 1715 and 1602 $cm^{-1}$.

(h) 2.38 g (5.5 mmoles) of 2R)-2-BOC-amino-2-diphenylmethoxycarbonylethoxycarbonyl chloride dissolved in 30 ml of absolute methylene chloride, followed by 0.4 ml (5 mmoles) of absolute pyridine, are added to a solution, cooled to 0°, of 3.26 g (5 mmoles) of 7β-[(2R,S)-2-(2-aminothiazol-4-yl)-2-BOC-aminoacetylamino]-3-methoxy-3-cephem-4-carboxylic acid diphenylmethyl ester in 75 ml of absolute methylene chloride, while stirring and in the absence of moisture. After an hour each at 0° and room temperature, the reaction mixture is diluted with methylene chloride (100 ml), washed with water (2×30 ml), dried ($Na_2SO_4$) and concentrated in a rotary evaporator. The crude product is purified over 30 times the amount of silica gel with diethyl ether/ethyl acetate as eluant. The 7β-{(2R,S)-2-[2-((2R)-2-BOC-amino-2-diphenylmethoxycarbonylethoxycarbonylamino)thiazol-4-yl]-2-BOC-aminoacetylamino}-3-methoxy-3-cephem-4-carboxylic acid diphenylmethyl ester obtained in amorphous form is used directly in the next synthesising step.

TLC: Rf=0.68 (eluant: ethyl acetate).

EXAMPLE 7

7β-[(2R,S)-2-(2-aminothiazol-4-yl)-2-aminoacetylamino]-3-methoxy-3-cephem-4-carboxylic acid 12 ml of trifluoroacetic acid are added to a solution, cooled to 0°, of 2.3 g of 7β-[(2R,S)-2-(2-aminothiazol-4-yl)-2-BOC-aminoacetylamino]-3-methoxy-3-cephem-4-carboxylic acid diphenylmethyl ester and 2.3 ml of anisole in 12 ml of absolute methylene chloride and the mixture is stirred for one hour, at room temperature, in the absence of moisture. After adding diethyl ether (200 ml) at 0°, the trifluoroacetate, obtained in solid form, is filtered off, washed with diethyl ether and dried in a high vaccum at room temperature. The aqueous solution (15 ml) of 7β-[(2R,S)-2-(2-aminothiazol-4-yl)-2-aminoacetylamino]-3-methoxy-3-cephem-4-carboxylic acid bis-trifluoroacetate is adjusted to a pH of 5.5 with 2 N sodium hydroxide solution at 0°, filtered clear and purified over Amberlite XAD-2 with water as eluant, whereupon, after removing the solvent in a rotary evaporator and drying in a high vacuum (16 hours at 0.05 torr and room temperature), the title compound, which contains 0.8 mole of water of crystallisation, is isolated in crystalline form.

M.p. from 145° C. (decomposition);
TLC: $Rf_{96}=0.1$;
$[\alpha]_D = +147° \pm 1°$ (c=0.805%, 0.1 N hydrochloric acid).

EXAMPLE 8

The following compounds may be produced in a manner analogous to the preceding Examples:

7β-{2-[2-((2R)-2-amino-2-carboxyethoxycarbonylamino)thiazol-4-yl]-2-syn-methoxyiminoacetylamino}-3-(4-carbamoylpyridinium)-methyl-3-cephem-4-carboxylate;

7β-{2-[2-((2R)-2-amino-2-carboxyethoxycarbonylamino)thiazol-4-yl]-2-hydroxyacetylamino}-3-acetoxymethyl-3-cephem-4-carboxylic acid;

7β-{2-[2-((2R)-2-amino-2-carboxyethoxycarbonylamino)thiazol-4-yl]-2-hydroxyacetylamino}-3-carbamoyloxymethyl-3-cephem-4-carboxylic acid;

7β-{2-[2-((2R)-2-amino-2-carboxyethoxycarbonylamino)thiazol-4-yl]-2-hydroxyacetylamino}-3-(1-methyl-1H-tetrazol-5-ylmethyl)-3-cephem-4-carboxylic acid;

7β-{2-[2-((2R)-2-amino-2-carboxyethoxycarbonylamino)thiazol-4-yl]-2-sulphoacetylamino}-3-acetoxymethyl-3-cephem-4-carboxylic acid;

7β-{2-[2-((2R)-2-amino-2-carboxyethoxycarbonylamino)thiazol-4-yl]-2-sulphoacetylamino}-3-carbamoyloxymethyl-3-cephem-4-carboxylic acid;

7β-{2-[2-((2R)-2-amino-2-carboxyethylthio-carbonylamino)thiazol-4-yl]-2-syn-methoxyiminoacetylamino}-3-acetoxymethyl-3-cephem-4-carboxylic acid;

7β-{2-[2-((2R)-2-amino-2-carboxyethylthio-carbonylamino)thiazol-4-yl]-2-syn-methoxyiminoacetylamino}-3-carbamoyloxymethyl-3-cephem-4-carboxylic acid;

and their sodium salts.

EXAMPLE 9

Dry ampoules or phials containing 0.5 g of sodium 7β-{2-[2-((2R)-2-amino-2-carboxyethoxycarbonylamino)thiazol-4-yl]-2-methoxyiminoacetylamino}-3-acetoxymethyl-3-cephem-4-carboxylate (1.6 H$_2$O) as active substance are produced as follows:

active substance: 0.5 g
mannitol: 0.05 g

A sterile aqueous solution of the active substance and mannitol is sealed under aseptic conditions in 5 ml ampoules or 5 ml phials and these are then examined.

EXAMPLE 10

Dry ampoules or phials containing 0.5 g of 7β-[(2R,S)-2-(2-aminothiazol-4-yl)-2-aminoacetylamino]-3-methoxy-3-cephem-4-carboxylic acid hydrate as active substance are obtained as follows:

Composition (for 1 ampoule or phial)
active substance: 0.5 g
mannitol: 0.05 g

A sterile aqueous solution of the active substance and mannitol is sealed under aseptic conditions in 5 ml ampoules or 5 ml phials and these are then examined.

What is claimed is:

1. Aminothiazolacetamido-3-cephem-4-carboxylic acid compounds of the formula

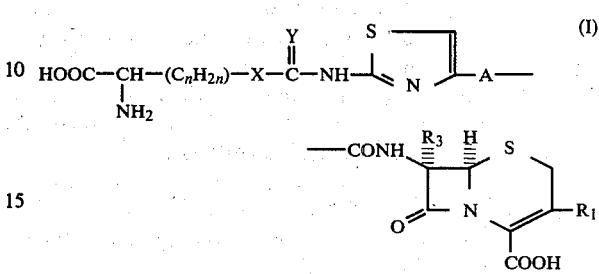

wherein the index n represents an integer of 1 to 4, X represents oxygen, sulphur, an —NH— group or the direct bond, Y represents oxygen or sulphur, A represents methylene or methylene substituted by amino, hydroxy, carboxyl, sulpho, oxo, or by the group =N—O—R$^o$ in which R$^o$ represents hydrogen, lower alkyl, or lower alkyl substituted by lower alkoxy, halogen, hydroxy, lower alkanoyloxy, sulfo, carboxy or lower alkoxycarbonyl, R$_1$ represents hydrogen, lower alkyl, lower alkoxy, halogen or a group of the formula —CH$_2$—R$_2$, in which R$_2$ represents lower alkanoyloxy, carbamoyloxy, N-lower alkylcarbamoyloxy, triazolylthio, tetrazolylthio, thiazolylthio, thiatriazolylthio, thiadiazolylthio, oxazolylthio, oxadiazolylthio or pyridinium, wherein the heterocyclic rings are unsubstituted or substituted by lower alkyl, N,N-di-lower alkylamino-lower alkyl, carboxy-lower alkyl, sulpholower alkyl, amino, carboxy-lower alkanoylamino or carbamoyl, and R$_3$ represents hydrogen or methoxy, and wherein the carboxyl groups are free or are esterified by lower alkanoyloxymethyl, aminolower alkanoyloxymethyl, phthalidyl or indanyl and pharmaceutically acceptable salts of such compounds.

2. The compounds of the formula I according to claim 1, in which the —(C$_n$—H$_{2n}$)— group is unbranched, n has the meaning given, X represents oxygen, sulphur or —NH—, Y represents oxygen, A represents methylene, aminomethylene, hydroxymethylene, carboxymethylene, sulphomethylene, hydroxyiminomethylene or methoxyiminomethylene, R$_1$ represents hydrogen, lower alkyl, lower alkoxy, halogen or a group of the formula —CH$_2$—R$_2$, in which R$_2$ represents lower alkanoyloxy, carbamoyloxy, N-lower alkylcarbamoyloxy, triazolylthio, tetrazolylthio, thiazolylthio, thiatriazolylthio, thiadiazolylthio, oxazolylthio, oxadiazolylthio or pyridinium, wherein the heterocyclic rings are unsubstituted or substituted, by lower alkyl, N,N-di-lower alkylamino-lower alkyl, carboxy-lower alkyl, sulpho-lower alkyl, amino, carboxy-lower alkanoylamino or carbamoyl, and R$_3$ represents hydrogen or methoxy, and pharmaceutically acceptable salts of such compounds.

3. Compounds of the formula I according to claim 1, in which the —(C$_n$H$_{2n}$)— group is unbranched, n has the meaning given, X represents oxygen, sulphur or —NH—, Y represents oxygen, A represents methylene, aminomethylene, hydroxymethylene or methoxyiminomethylene, R$_1$ represents hydrogen, methyl, methoxy, chlorine, or a group of the formula —CH$_2$—R$_2$, in which R₂ represents acetoxy, carbamoyloxy, 1-methyl-1H-tetrazol-5-ylthio, 1-sulphomethyl-1H-tetrazol-5-ylthio, 1-carboxymethyl-1H-tetrazol-5-ylthio, 1-(2-dimethylaminoethyl)-1H-tetrazol-5-ylthio, 2-methyl-1,3,4-thiadiazol-5-ylthio, or 4-carbamoylpyridinium, and R₃ represents hydrogen, and pharmaceutically acceptable salts of such compounds.

4. The sodium salts of the compounds of formula I according to claim 1.

5. 7β-{2-[2-((2R)-2-amino-2-carboxyethoxycarbonylamino)thiazol-4-yl]acetylamino}-3-acetoxymethyl-3-cephem-4-carboxylic acid according to claim 1.

6. 7β-{2-[2-((2R)-2-amino-2-carboxyethoxycarbonylamino)thiazol-4-yl]-2-syn-methoxyiminoacetylamino}-3-acetoxymethyl-3-cephem-4-carboxylic acid according to claim 1.

7. 7β-{2-[2-((2R)-amino-2-carboxyethoxycarbonylamino)thiazol-4-yl]-2-syn-methoxyiminoacetylamino}-3-carbamoyloxymethyl-3-cephem-4-carboxylic acid according to claim 1.

8. 7β-{2-[2-((2R)-2-amino-2-carboxyethoxycarbonylamino)thiazol-4-yl]-2-syn-methoxyiminoacetylamino}-3-methoxy-3-cephem-4-carboxylic acid according to claim 1.

9. 7β-{2-[2-((2R)-2-amino-2-carboxyethoxycarbonylamino)thiazol-4-yl]-2-syn-methoxyiminoacetylamino}-3-[(1-methyl-1H-tetrazol-5-yl)thiomethyl]-3-cephem-4-carboxylic acid according to claim 1.

10. 7β-{(2R,S)-2-[2-((2R)-2-amino-2-carboxyethoxycarbonylamino)thiazol-4-yl]-2-aminoacetylamino}-3-methoxy-3-cephem-4-carboxylic acid according to claim 1.

11. A pharmaceutical preparation containing an effective amount of a compound of formula I according to claim 1, together with pharmaceutically acceptable carriers.

12. Method for treating infections caused by gram-positive and gram-negative bacteria, which comprises administering a pharamceutical preparation according to claim 11.

* * * * *